United States Patent
Ali et al.

(10) Patent No.: US 10,058,856 B2
(45) Date of Patent: *Aug. 28, 2018

(54) METHOD FOR PALLADIUM-CATALYZED CINAMMIC ACID FORMATION

(71) Applicant: KING FAHD UNIVERSITY OF PETROLEUM AND MINERALS, Dhahran (SA)

(72) Inventors: Bassam El Ali, Dhahran (SA); Mansur B. Ibrahim, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/919,669

(22) Filed: Mar. 13, 2018

(65) Prior Publication Data

US 2018/0200705 A1  Jul. 19, 2018

Related U.S. Application Data

(63) Continuation of application No. 15/257,466, filed on Sep. 6, 2016, now Pat. No. 9,956,550.

(51) Int. Cl.

| | |
|---|---|
| *C07C 63/64* | (2006.01) |
| *B01J 31/22* | (2006.01) |
| *B01J 35/02* | (2006.01) |
| *C07C 51/377* | (2006.01) |

(52) U.S. Cl.
CPC ......... *B01J 31/2295* (2013.01); *B01J 35/026* (2013.01); *C07C 51/377* (2013.01); *B01J 2231/4261* (2013.01); *B01J 2531/824* (2013.01)

(58) Field of Classification Search
CPC .................................................. B01J 31/2295
USPC .......................................................... 562/495
See application file for complete search history.

(56) References Cited

U.S. PATENT DOCUMENTS

| | | |
|---|---|---|
| 6,417,357 B1 | 7/2002 | Tinkl et al. |
| 6,455,725 B1 | 9/2002 | Lange |
| 2018/0065117 A1* | 3/2018 | Ali ....................... B01J 31/2295 |

OTHER PUBLICATIONS

V. Polshettiwar et al., "PdeN-heterocyclic carbine (NHC) organic silica: synthesis and application in carbon-carbon coupling reactions" Tetrahedron, vol. 64, 2008, pp. 4637-4643.

T. Suzuka et al., "Reusable Polymer-Supported Terpyridine Palladium Complex for Suzuki-Miyaura, Mizoroki-Heck, Sonogashira, and Tsuji-Trost Reaction in Water" Polymers, vol. 3, 2011, pp. 621-639.

M. Bakherad et al., "Solvent-free Heck and copper-free Sonogashirac ross-coupling reactions catalyzed by a polystyrene-anchored Pd(II) phenyldithiocarbazate complex" Tetrahedron Letters, vol. 53, 2012, pp. 5773-5776.

(Continued)

*Primary Examiner* — Deborah D Carr
(74) *Attorney, Agent, or Firm* — Oblon, McClelland, Maier & Neustadt, L.L.P.

(57) ABSTRACT

A solid-supported palladium(II) complex which catalyzes the Mizoroki-Heck coupling reaction efficiently and a method of employing the solid-supported palladium(II) complex to synthesize cinnamic acid and derivatives thereof. The solid-supported palladium(II) complex is also stable and can be recycled without significantly losing catalytic activity.

5 Claims, 10 Drawing Sheets

(56) References Cited

OTHER PUBLICATIONS

S.M. Sarkar et al., "Pyridinyl functionalized MCM-48 supported highly active heterogeneous palladium catalyst for cross-coupling reactions" RSC Advances, vol. 5, 2015, pp. 19630-19637.

E. Mieczynska et al., "Selective Heck Arylation of Cyclohexene with Homogeneous and Heterogeneous Palladium Catalysts" Molecules. vol. 15, 2010, pp. 2166-2177.

S.Huang et al., "Palladium(II)/Cationic 2,2'-Bipyridyl System as a Highly Efficient and Reusable Catalyst for the Mizoroki-Heck Reaction in Water" Molecules, vol. 15, 2010, pp. 315-330.

A.Ohtaka et al., "Linear Polystyrene-Stabilized PdO Nanoparticle-Catalyzed Mizoroki-Heck Reactions in Water" Molecules, vol. 16, 2011, pp. 9067-9076.

M.Islam et al., "Heterogeneously Catalyzed Phosphine-Free Heck Cross-Coupling Reaction of Aryl Halides with Reusable Palladium(II) Schiff Base Complex" J.Braz. Chem. Soc., vol. 22, 2011, pp. 319-326.

L.E.O'Leary et al., "Heck Coupling of Olefins to Mixed Methyl/Thienyl Monolayers on Si(111) Surfaces" Journal of the American Chemical Society, 2013, pp. 10081-10090.

M.B. Ibrahim et al., "Effective palladium(II)-bis(oxazoline) catalysts: synthesis, crystal structure, and catalytic coupling reactions" Journal of Coordination Chemistry, 2015, pp. 431-448.

M.B.Ibrahim et al., "A highly active palladium(II)-bis(oxazoline) catalyst for Suzuki-Miyaura,Mizoroki-Heck and sonogashira coupling reactions in aqueous dimethylformamide" Applied Organometallic Chemistry, vol. 29, 2015, pp. 400-407.

Ibrahim ("A palladium-bisoxazoline supported catalyst for selective synthesis of aryl esters and aryl amides via carbonylative coupling reactions" RSC Advances, first published on Aug. 15, 2016, vol. 6, p. 78826) (Year: 2016).

Hallman ("Polymer-bound bis(oxazoline) as a chiral catalyst" Tetrahedron: Asymmetry 12, 2001, p. 1475-1478) (Year: 2001).

Gruber-Woelfler ("Synthesis, catalytic activity, and leaching studies of a heterogeneous Pd-catalyst including an immobilized bis(oxazoline) ligand" Journal of Catalysis 286, 2012, p. 30-40) (Year: 2012).

\* cited by examiner

Pd3d Scan

Pd3d Scan

METHOD FOR PALLADIUM-CATALYZED CINAMMIC ACID FORMATION

CROSS-REFERENCE TO RELATED APPLICATIONS

The present application is a Continuation of Ser. No. 15/257,466, having a filing date of Sep. 6, 2016.

STATEMENT OF FUNDING ACKNOWLEDGEMENT

This project was funded by the National Plan for Science, Technology and Innovation (MARIFAH)—King Abdulaziz City for Science and Technology—through the Science & Technology Unit at King Fahd University of Petroleum & Minerals (KFUPM), the Kingdom of Saudi Arabia, award number (14-PET2737-04).

BACKGROUND OF THE INVENTION

Technical Field

The present disclosure relates to a solid-supported palladium(II) complex which catalyzes the Mizoroki-Heck coupling reaction and a method of employing the solid-supported palladium(II) complex to synthesize cinnamic acid and derivatives thereof.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Among metal catalysts, palladium complexes have been used widely due to their versatility in modern organic synthesis (e.g. in synthetic transformations including Mizoroki-Heck, Suzuki, Stille and Sonogashira cross coupling reactions) (J. H. Kim, J. S. Park, H. W. Chung, B. W. Boote, T. R. Lee, RSC Adv. 2 (2012) 3968-3977; B. Tamami, H. Allahyari, S. Ghasemi, F. Farjadian, J. Organomet. Chem. 696 (2011) 594-599; A. F. Lee, P. J. Ellis, I. J. S. Fairlamb, K. Wilson, Dalton Trans. 39 (2010) 10473-10482; and X. Gao, N. Zhao, M. Shu, S. Che, Appl. Catal. A: Gen. 388 (2010) 196-201, each incorporated herein by reference in their entirety).

Homogeneous palladium catalysts, however, suffer from the problems associated with the need and handling of sensitive ligands. Such catalysts are also difficult to recover and to separate from the coupling products, making it a challenge to recycle the expensive palladium.

The separation and recycling of homogeneous transition metal catalysts remain the most serious scientific and commercial challenges in the area of catalysis. The difficulty in the separation and recycling processes of the transition metal catalysts has limited their practical uses for application in the fine chemical industry (Herrmann, W. A.; Cornils, B. Angew. Chem., Int. Ed. 1997, 36, 1048; Baker, R. T.; Tumas, W. Science 1999, 284, 1477; Cole-Hamilton, D. J. Science 2003, 299, 1702; and Herrmann, W. A. Applied Homogeneous Catalysis with Organometallic Compounds; Cornils, B., Herrmann, W. A., Eds.; VCH: Weinheim, Germany, 1996; Vol. 2, p 712, each incorporated herein by reference in their entirety).

Therefore, many strategies for effective catalyst recycling have been explored, including supported aqueous-phase catalysis, fluorous-phase catalysis, and the use of ionic liquids and supercritical fluids (Arhanchet, J. P.; Davis, M. E.; Merola, J. S.; Hanson, B. E. Nature 1989, 339, 454; Davis, M. E. CHEMTECH 1992, 498; Sandee, A. J.; Slagt, V. F.; Reek, J. N. H.; Kamer, P. C. J.; van Leeuwen, P. W. N. M. Chem. Commun. 1999, 1633; Barthel-Rosa, L. P.; Gladysz, J. A. Coord. Chem. Rev. 1999, 190-192, 587; Rocaboy, C.; Rutherford, D.; Bennett, B. L.; Gladysz, J. A. J. Phys. Org. Chem. 2000, 13, 596; Richter, B.; Spek, A. L.; van Koten, G.; Deelman, B.-J. J. Am. Chem. Soc. 2000, 122, 3945; de Wolf, E.; van Koten, G.; Deelman, B.-J. Chem. Soc. Rev. 1999, 28, 37; Wasserscheid, P.; Welton, T. Ionic Liquids in Synthesis; Wiley-VCH: Weinheim, Germany, 2003; Wasserscheid, P.; Waffenschmidt, H.; Machnitzki, P.; Kottsieper, K. W.; Stelzer, O. Organometallics 2000, 19, 3818; Bronger, R. P. J.; Silva, S. M.; Kamer, P. C. J.; van Leeuwen, P. W. N. M. Chem. Commun. 2002, 3044; Wasserscheid, P.; Waffenschmidt, H.; Machnitzki, P.; Kottsieper, K. W.; Stelzer, O. Chem. Commun. 2001, 451; Jessop, P. G.; Ikariya, T.; Noyori, R. Chem. Rev. 1999, 99, 475; Leitner, W. Acc. Chem. Res. 2002, 35, 746, each incorporated herein by reference in their entirety).

Hence, the support of homogeneous catalysts and the application of supported catalysts in fine chemical synthesis has become a major area of research in chemistry due to the advantages of such catalysts over the homogeneous catalysts and the positive impact on the environment (Clark, J. H.; Macquarrie, D. J. Handbook of Green Chemistry and Technology; Blackwell: Oxford, 2002; and Anastas, P. T.; Kirchhoff, M. M.; Williamson, T. C. Appl. Catal., A 2001, 221, 3, each incorporated herein by reference in their entirety). Therefore, there is a demand to develop heterogeneous palladium catalysts for industrial applications.

The Mizoroki-Heck reaction is among the most important and widely used reactions for the formation of carbon-carbon bond, which allows the arylation, alkylation or vinylation of various alkenes through their reaction with aryl, vinyl, benzyl, or allyl halides in the presence of palladium and a suitable base in a single step under mild conditions (Beletskaya, I. P.; Cheprakov, A. V. Chem. Rev. 2000, 100, 3009; Mizoroki-Heck, R. F. Palladium Reagents in Organic Synthesis; Academic: London, 1985; Trzeciak, A. M.; Ziolkowski, J. J. Coord. Chem. Rev. 2005, 249, 2308; and Alonso, F.; Beletskaya, I. P.; Yus, M. Tetrahedron 2005, 61, 11771, each incorporated herein by reference in their entirety). There are some examples of the application of the Mizoroki-Heck coupling reaction on the industrial scale (Eisenstadt, A.; Ager, D. J. Fine Chemicals through Heterogeneous Catalysis; Sheldon, R. A., van Bekkum, H., Eds.; Wiley-VCH: Weinheim, 2001; p 576; and Zapf, A.; Beller, M. Top. Catal. 2002, 19, 101; and Tucker, C. E.; de Vries, J. G. Top. Catal. 2002, 19, 111, each incorporated herein by reference in their entirety).

Therefore, an objective of the present disclosure is to provide a solid-supported palladium(II) catalyst effective for Mizoroki-Heck coupling reactions. It is a further objective to provide a method of employing the solid-supported palladium(II) catalyst.

BRIEF SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

A first aspect of the disclosure relates to a solid-supported ligand, comprising a reaction product of:
a ligand of formula (I)

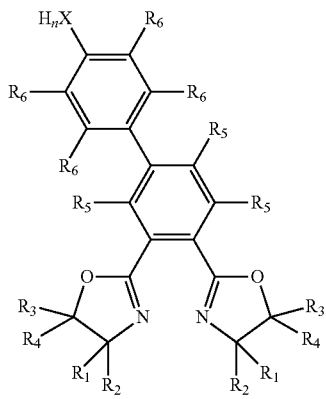

(I)

or a salt, solvate, or stereoisomer thereof, and
a solid support comprising silica,
where the solid support is functionalized to comprise a substituted benzyl,
a X atom in the compound of formula (I) is bonded to a carbon atom of the solid support,
$R_1$, $R_2$, $R_3$, and $R_4$ are independently H, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted heteroarylcarbonyl, an optionally substituted hydrocarbyl, an optionally substituted arylolefin, an optionally substituted arylalkylcarboxylic acid, or an optionally substituted vinyl,
each $R_5$ and $R_6$ is independently H, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted heteroarylcarbonyl, an optionally substituted hydrocarbyl, an optionally substituted arylolefin, an optionally substituted arylalkylcarboxylic acid, or an optionally substituted vinyl, and
n is 1 with the proviso that X is O or S, or
n is 2 with the proviso that X is N.
In one embodiment, $R_1$ and $R_2$ are $CH_3$, $R_3$, $R_4$, $R_5$, and $R_6$, are H, n is 1, X is O, and the solid support is silica gel.
In one embodiment, the solid support is in the form of a particle with an average diameter of 1-100 μm.

A second aspect of the disclosure relates to a solid-supported catalyst, comprising a reaction product of the solid-supported ligand of the first aspect, and a palladium(II) salt of the formula $PdZ_2$, where the reaction product comprises a palladium(II) ion bound to a nitrogen atom in each oxazoline heterocycle, and Z is selected from the group consisting of Cl, I, Br, OAc, and OTf.

In one embodiment, $R_1$ and $R_2$ are $CH_3$, $R_3$, $R_4$, $R_5$, and $R_6$ are H, n is 1, X is O, the solid support is silica gel, and Z is Cl.

In one embodiment, the solid support is in the form of a particle with an average diameter of 1-100 μm.

In one embodiment, the solid-supported catalyst comprises 0.1-1 mmol of palladium per gram of the solid-supported catalyst.

In one embodiment, the solid-supported catalyst has a turnover number in a range of 1,500-2,500 and a turnover frequency in a range of 200-1,500 per hour.

A third aspect of the disclosure relates to a method for synthesizing cinnamic acid or derivatives thereof, the method comprising reacting an aryl halide with an acrylic acid or derivatives thereof in the presence of a solvent, a base, and the solid-supported catalyst of the second aspect at a temperature in a range of 35-110° C., thereby forming the cinnamic acid or derivatives thereof.

In one embodiment, the method further comprises separating the solid-supported catalyst from the cinnamic acid or derivatives thereof, and reusing the solid-supported catalyst in at least two cycles, where the solid-supported catalyst loses less than 5 wt % of the palladium after the at least two cycles.

In one embodiment, the aryl halide is a limiting reactant.
In one embodiment, an amount of the solid-supported catalyst is in a range of 0.05-10 mol % relative to a number of moles of the aryl halide.

In one embodiment, the solvent comprises 5-95% by volume of water and 5-95% by volume of an organic solvent, based on a total volume of the solvent.

In one embodiment, the organic solvent is dimethyl formamide.

In one embodiment, the base is at least one selected from the group consisting of an alkali metal hydroxide, an alkali metal carbonate, and an amine.

In one embodiment, the cinnamic acid or derivatives thereof comprises less than 10 ppb palladium, based on a total weight of the cinnamic acid or derivatives thereof.

A fourth aspect of the disclosure relates to a method for synthesizing cinnamic acid or derivatives thereof, the method comprising reacting an aryl halide with an acrylic acid or derivatives thereof in the presence of a solvent, a base, and the solid-supported catalyst of the second aspect with $R_1$ and $R_2$ are $CH_3$, $R_3$, $R_4$, $R_5$, and $R_6$ are H, X is O, SS is silica gel, and Z is Cl at a temperature in a range of 35-110° C., thereby forming the cinnamic acid or derivatives thereof.

In one embodiment, the method further comprises separating the solid-supported catalyst from the cinnamic acid or derivatives thereof, and reusing the solid-supported catalyst in at least two cycles, wherein the solid-supported catalyst loses less than 5 wt % of the palladium after the at least two cycles.

In one embodiment, the cinnamic acid or derivatives thereof comprises less than 10 ppb palladium, based on a total weight of the cinnamic acid or derivatives thereof.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
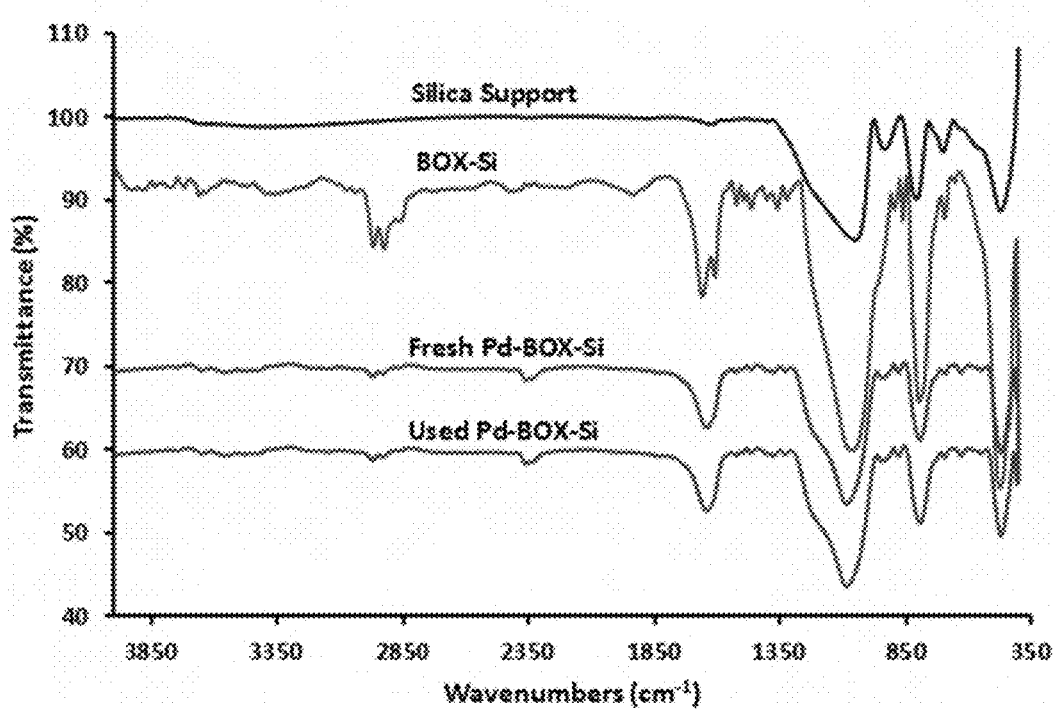
FIG. 1 is an overlay of the FT-IR spectra of unmodified 4-benzyl chloride functionalized silica support "Silica Support", silica-supported BOX ligand "BOX-Si", silica-supported Pd-BOX catalyst "Fresh Pd-BOX-Si", and used silica-supported Pd-BOX catalyst "Used Pd-BOX-Si" recovered from Mizoroki-Heck coupling reaction.

Embodiments of the present disclosure will now be described more fully hereinafter with reference to the accompanying drawings, in which some, but not all of the embodiments of the disclosure are shown.

The present disclosure will be better understood with reference to the following definitions.

As used herein, the words "a" and "an" and the like carry the meaning of "one or more".

As used herein, the terms "compound", "complex", and "catalyst" are used interchangeably, and are intended to refer to a chemical entity, whether in the solid, liquid or gaseous phase, and whether in a crude mixture or purified and isolated. As used herein, the term "ligand" refers to an organic molecule comprising at least a phenyl ring, and two oxazoline groups bound separately to the phenyl ring via a C—C bond and arranged ortho to one another, and each oxazoline group comprises a nitrogen atom which can bind to the palladium(II) ion covalently thereby forming a chelate.

The term "alkyl", as used herein, unless otherwise specified, refers to a straight, branched, or cyclic hydrocarbon fragment. Non-limiting examples of such hydrocarbon fragments include methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. As used herein, the term "cyclic hydrocarbon" refers to a cyclized alkyl group. Exemplary cyclic hydrocarbon (i.e. cycloalkyl) groups include, but are not limited to, cyclopropyl, cyclobutyl, cyclopentyl, cyclohexyl, norbornyl, and adamantyl. Branched cycloalkyl groups, such as exemplary 1-methylcyclopropyl and 2-methycyclopropyl groups, are included in the definition of cycloalkyl as used in the present disclosure.

The term "aryl", as used herein, and unless otherwise specified, refers to phenyl, biphenyl, naphthyl, anthracenyl, and the like. The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

As used herein, the term "substituted" refers to at least one hydrogen atom that is replaced with a non-hydrogen group, provided that normal valencies are maintained and that the substitution results in a stable compound. When a compound or a R group (denoted as $R_1$, $R_2$, and so forth) is noted as "optionally substituted", the substituents are selected from the exemplary group including, but not limited to, aroyl (as defined hereinafter), halogen (e.g. chlorine, bromine, fluorine or iodine), alkyl, alkoxy (i.e. straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decyloxy), cycloalkyloxy including cyclopentyloxy, cyclohexyloxy, and cycloheptyloxy, aryloxy including phenoxy and phenoxy substituted with halo, alkyl, alkoxy, and haloalkyl which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl, hydrocarbyl, substituted hydrocarbyl, arylalkyl, hydroxy, alkoxy, oxo, alkanoyl, alkanoyloxy, amino, alkylamino, arylamino, arylalkylamino, disubstituted amines (e.g. in which the two amino substituents are selected from the exemplary group including, but not limited to, alkyl, aryl, or arylalkyl), alkanylamino, arylamino, alkanoylamino, substituted alkanoylamino, substituted arylamino, substituted arylamino, thiol, alkylthio, arylthio, arylalkylthio, alkylthiono, arylthiono, aryalkylthiono, alkylsulfonyl, arylsulfonyl, arylalkylsulfonyl, sulfonamido (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or arylalkyl), alkoxycarbonyl, aryl, substituted aryl, guanidine, heteroarylcarbonyl, substituted heteroarylcarbonyl, heterocyclyl, substituted heterocyclyl and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety).

The term "heterocyclyl" as used in this disclosure refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl and azepanyl. Examples of such bicyclic rings include indolinyl, isoindolinyl, benzopyranyl, quinuclidinyl, 2,3,4,5-tetrahydro-1,3,benzazepine, 4-(benzo-1,3,dioxol-5-methyl)piperazine, and tetrahydroisoquinolinyl. Further, "substituted heterocyclyl" may refer to a heterocyclyl ring which has one or more oxygen atoms bonded to the ring (i.e. as ring atoms). Preferably, said atom which is bonded to the ring selected from nitrogen or sulphur. An example of a heterocyclyl substituted with one or more oxygen atoms is 1,1-dioxido-1,3-thiazolidinyl.

The term "alkylthio" as used in this disclosure refers to a divalent sulfur with alkyl occupying one of the valencies and includes the groups methylthio, ethylthio, propylthio, butylthio, pentylthio, hexylthio, octylthio.

The term "alkanoyl" as used in this disclosure refers to an alkyl group having 2 to 18 carbon atoms that is bound with a double bond to an oxygen atom. Examples of alkanoyl includes, acetyl, propionyl, butyryl, isobutyryl, pivaloyl, valeryl, hexanoyl, octanoyl, lauroyl, stearoyl.

The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl.

Examples of aroyl are benzoyl and naphthoyl, and "substituted aroyl" may refer to benzoyl or naphthoyl substituted by at least one substituent including those selected from halogen, amino, vitro, hydroxy, alkyl, alkoxy and haloalkyl on the benzene or naphthalene ring.

The term "heteroarylcarbonyl" as used in this disclosure refers to a heteroaryl moiety with 5 to 10 membered mono- or fused-heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, benzimidazolyl-carbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus, and includes, for example, 2-oxo-1,3-dioxolan-4-ylmethyl, 2-oxo-1,3-dioxan-5-yl.

Vinyl refers to an unsaturated substituent having at least one unsaturated double bond and having the formula $CH_2=CH-$. Accordingly, said "substituted vinyl" may refer to the above vinyl substituent having at least one of the protons on the terminal carbon atom replaced with alkyl, cycloalkyl, cycloalkylalkyl, aryl, substituted aryl, heteroaryl or substituted heteroaryl.

The term "hydrocarbyl" as used herein refers to a univalent hydrocarbon group containing up to about 24 carbon atoms (i.e., a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

As used herein, the term "derivative" refers to a chemically modified version of a chemical compound that is structurally similar to a parent compound.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

As used herein, the term "solvent" includes, but is not limited to, water (e.g. tap water, distilled water, doubly distilled water, deionized water, deionized distilled water), organic solvents, such as ethers (e.g. diethyl ether, tetrahydrofuran, 1,4-dioxane, tetrahydropyran, t-butyl methyl ether, cyclopentyl methyl ether, di-iso-propyl ether), glycol ethers (e.g. 1,2-dimethoxyethane, diglyme, triglyme), alcohols (e.g. methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), aromatic solvents (e.g. benzene, o-xylene, m-xylene, p-xylene, and mixtures of xylenes, toluene, mesitylene, anisole, 1,2-dimethoxybenzene, α,α,α,-trifluoromethylbenzene, fluorobenzene), chlorinated solvents (e.g. chlorobenzene, dichloromethane, 1,2-dichloroethane, 1,1-dichloroethane, chloroform), ester solvents (e.g. ethyl acetate, propyl acetate), amide solvents (e.g. dimethylformamide, dimethylacetamide, N-methyl-2-pyrrolidone), urea solvents, ketones (e.g. acetone, butanone), acetonitrile, propionitrile, butyronitrile, benzonitrile, dimethyl sulfoxide, ethylene carbonate, propylene carbonate, 1,3-dimethyl-3,4,5,6-tetrahydro-2(1H)-pyrimidinone, and mixtures thereof.

As used herein, the term "base" includes, but is not limited to, an alkali metal hydride (e.g. sodium hydride, potassium hydride), an alkali metal hydroxide (e.g. lithium hydroxide, potassium hydroxide, sodium hydroxide, cesium hydroxide), an alkali metal carbonate (e.g. lithium carbonate, potassium carbonate, sodium carbonate, cesium carbonate), an alkali metal acetate (e.g. lithium acetate, sodium acetate, potassium acetate), an amine (e.g. trialkylamine of formula $NR'_3$ (where each R' may be independently ethyl, n-propyl, and n-butyl) and dialkylamine of formula $HNR'_2$, or mixtures thereof, diethylamine, di-n-butylamine, pyrrolidine, piperidine, triethylamine, tri-n-butylamine, diisopropylethylamine, dicyclohexylmethylamine, pyridine, 2,6-dimethylpyridine, 4-aminopyridine, N-methyl-2,2,6,6-tetramethylpiperidine, 2,2,6,6-tetramethylpiperidine, 2,6-di-tert-butylpyridine, 1,4-diazabicyclo[2.2.2]octane), and mixtures thereof. The presence of a base is often important for the palladium-catalyzed Mizoroki-Heck coupling reaction in order to neutralize the hydrogen halide produced as the byproduct of the coupling reaction (Chih-chung, T.; Mungyuen, L.; Bingli, M.; Sarah, W.; Alan, S. C.; Chem. Lett. 2011, 40:9 955. Thorwirth, R.; Stolle, A.; Ondruschka, B.; Green Chem. 2010, 12, 985. Bakherad, M.; Keivanloo, A.; Samangooei, S.; Omidian, M. J. Organometal. Chem. 2013, 740, 78. Feng, Z.; Yu, S.; Shang, Y. Appl. Organometal. Chem. 2008, 22, 577. Shingo, A.; Motohiro, S.; Yuki, S.; Hirojiki, S.; Takuya, Y.; Aiky, O. Chem. Lett. 2011, 40:9, 925. Korzec, M.; Bartczak, P.; Niemczyk, A.; Szade, J.; Kapkowski, M.; Zenderowska, P.; Balin, K.; Lelarko, J.; Polariski, J. J. Catal. 2014, 313, 1. Zhang, G.; Luan, Y.; Han, X.; Wang, Y.; Wen, X.; Ding, C. Appl. Organometal. Chem. 2014, 28, 332, each incorporated herein by reference in their entirety).

As used herein, the term "palladium(II) salt" includes, but is not limited to, palladium(II) chloride, palladium(II) bromide, palladium(II) iodide, bis(benzonitrile) palladium(II) chloride, bis(acetonitrile)palladium(II) chloride, and palladium(II) acetate.

A first aspect of the disclosure relates to a solid-supported ligand, comprising a reaction product of:
a ligand of formula (I)

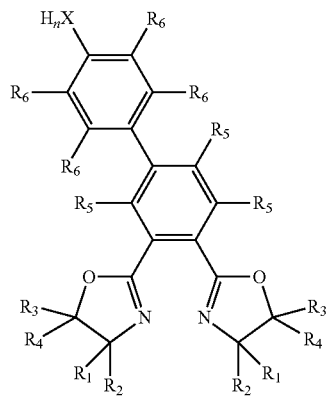

(I)

or a salt, solvate, or stereoisomer thereof, and
a solid support comprising silica,
where the solid support may be functionalized to comprise a substituted benzyl, a X atom in the compound of formula (I) is bonded to a carbon atom of the solid support, and n is 1 with the proviso that X is O or S, or n is 2 with the proviso that X is N.

The solid support functionalized with an optionally substituted benzyl may be represented by the following formula:

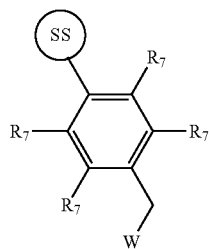

where SS is the solid support, and W may be Cl, Br, or I.

The solid-supported ligand may be represented by the following formula:

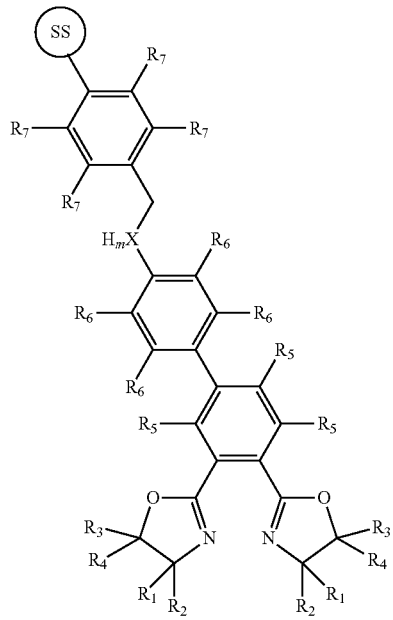

where m is 1 with the proviso that X is N, or m=0 (i.e. no H) with the proviso that X is O or S.

Substituents $R_1$, $R_2$, $R_3$, and $R_4$ may be independently H, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted heteroarylcarbonyl, an optionally substituted hydrocarbyl, an optionally substituted arylolefin, an optionally substituted arylalkylcarboxylic acid, or an optionally substituted vinyl.

Each $R_5$, $R_6$, and $R_7$ may be independently H, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted heteroarylcarbonyl, an optionally substituted hydrocarbyl, an optionally substituted arylolefin, an optionally substituted arylalkylcarboxylic acid, or an optionally substituted vinyl.

The optionally substituted alkyl group may comprise 1-8 carbon atoms, preferably 1-5 carbon atoms, more preferably 1-3 carbon atoms. In one embodiment, the optionally substituted alkyl group comprises 1 carbon atom and is a methyl group. The optionally substituted aryl group is preferably a phenyl group. The alkyl and aryl groups may be substituted with the aforementioned substituents. Preferably, the alkyl and/or the aryl groups are substituted with hydroxyl, alkoxy, aryloxy, nitro, or cyano, either unprotected, or protected as necessary.

In another embodiment, $R_1$, $R_2$, $R_3$, $R_4$, $R_5$, $R_6$, and $R_7$ may be independently a halogen atom, a hydroxyl, a nitro, a cyano, an optionally substituted heterocyclyl, an optionally substituted arylalkyl, an optionally substituted heteroaryl, or an optionally substituted alkoxyl. The optionally substituted heterocyclyl may be a derivative of an O-heterocyclyl such as tetrahydrofuran, tetrahydropyran, or dioxane. The optionally substituted heteroaryl may be a derivative of an O-heteroaromatic compound such as furan. The optionally substituted arylalkyl may be, but is not limited to, benzyl, phenethyl, and phenylpropyl. The optionally substituted alkoxyl may be, but is not limited to, methoxy, ethoxy, and phenoxyl.

In some embodiments, $R_1$ and $R_2$ may not be an amino, an alkylamino, an arylamino, a N-monosubstituted amino, a N,N-disubstituted amino, a thiol or an optionally substituted thioalkoxyl because these groups contain nucleophilic atoms that may poison the catalyst. As used herein, the term "poisoning" refers to the nucleophilic atom(s) coordinating strongly to the palladium ion and thereby reducing the effectiveness of the catalyst.

The recycling of homogeneous catalysts is complex and costly. Therefore, the use of immobilized catalysts is a good option for industries to combine the advantages of both homogeneous and heterogeneous catalysts and also to overcome the problem related to metal contamination (Polshettiwar, V.; Len, C.; Fihri, A. Coord. Chem. Rev. 2009, 253, 2599; Hallamn, K.; Moberg, C. *Tetrahedron: Asymmetry*, 2001, 12, 1475, incorporated herein by reference in its entirety).

The solid support may be in a form of a particle with a shape of a sphere, ellipsoid, cube, cuboid, cylindrical, or polygonal prism (e.g. triangular prism, hexagonal prism, and pentagonal prism). In a preferred embodiment, the solid support particle has an irregular shape. An average diameter of the solid support particle may be in a range of 1-100 µm, preferably 20-80 µm, more preferably 35-75 µm. In other embodiments, the average diameter of the solid support particle is in a range of 0.5-1,000 nm, preferably 1-500 nm, more preferably 5-100 nm. For spherical, ellipsoidal, or irregularly-shaped particles, the term "diameter" refers to a longest straight-line distance between two points on a surface of the particle. A surface area of the solid support particle may range from 100-2,000 m$^2$/g, preferably 300-1,000 m$^2$/g, more preferably 500-1,000 m$^2$/g. The solid support particle may comprise pores with an average diameter in a range of 0.5-50 nm, preferably 0.5-30 nm, more preferably 0.5-10 nm. A porosity of the solid support may be in a range of 1-99%, preferably 20-90%, more preferably 40-80%. In one embodiment, the solid support is non-porous.

The solid support may comprise at least 10 wt %, preferably at least 50 wt %, more preferably at least 70 wt % silica, more preferably at least 80 wt % silica, more preferably at least 90 wt % silica, more preferably at least 95 wt % silica, more preferably at least 99 wt % silica, based on a total weight of the solid support. Exemplary solid support includes, without limitation, zeolite/aluminum silicate (e.g. andalusite, kyanite, sillimanite, kaolinite, metakaolinite, 3:2 mullite, 2:1 mullite), amorphous silica, crystalline silica, fibrous silica, precipitated silica, mesoporous silica (e.g. MCM-41 and SBA-15), fumed silica, silica-alumina, and silica gel.

The solid support may be functionalized to facilitate a covalent attachment of the ligand. The term "functionalize" refers to the modification of a surface of the solid support particle with an organic moiety containing carbon. Exemplary organic moiety includes, without limitation, 4-benzyl chloride, 3-aminopropyl, 4-bromopropyl, 4-bromophenyl, 3-carboxypropyl, 2-(carbomethoxy)propyl, 3-chloropropyl, 3-(2-succinic anhydride)propyl, 1-(allyl)methyl, 3-(thio-cyano)propyl, 3-(isocyano)propyl, propionyl chloride, 3-(maleimido)propyl, 3-(glycidoxy)propyl, 4-ethyl benzenesulfonyl chloride, 2-(3,4-epoxycyclohexyl)propyl, and 3-propylsulfonic acid, preferably 4-benzyl chloride. A loading of the organic moiety on the solid support may be in a range of 1-10 mmol/g, preferably 1-5 mmol/g, more preferably 1-3 mmol/g.

In a preferred embodiment, $R_1$ and $R_2$ are $CH_3$, $R_3$, $R_4$, $R_5$, $R_6$, and $R_7$ are H, m is 0, X is O, and the solid support (or SS) is silica gel.

A preparation of the precursor to the ligand is described hereinafter. A solution of 4-halophthalonitrile of the following structure:

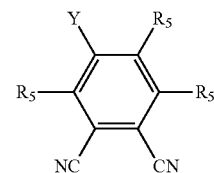

where Y is I, Br, or Cl, preferably I, and a triflate salt (e.g. zinc triflate) in dried chlorobenzene is stirred at room temperature for 15 min. An amount of 4-halophthalonitrile is in a range of 1-20 mmol, preferably 1-10 mmol, more preferably 1-5 mmol. In some embodiments, other triflate salts such as lanthanide triflates of the formula $Ln(OTf)_3$ (where Ln=La, Ce, Pr, Nd, Sm, Eu, Gd, Tb, Dy, Ho, Er, Tm, Yb, Lu, Y) and scandium triflate are used. An amount of triflate salt is in a range of 0.1-1 mmol, preferably 0.1-0.5 mmol, more preferably 0.1-0.3 mmol, and 1-10 mol % relative to the number of moles of the 4-halophthalonitrile, preferably 1-8 mol %, more preferably 3-6 mol %. Preferred organic solvents include, without limitation, benzene, toluene, p-xylene, o-xylene, and m-xylene. An amount of the organic solvent is in a range of 5-50 ml, preferably 10-40 ml, more preferably 20-40 ml. The solution may be stirred for 5-60 minutes, preferably 5-30 minutes, more preferably 10-20 minutes at a temperature in a range of 10-40° C., preferably 15-30° C., more preferably 20-30° C.

A solution of a β-amino alcohol of the following structure:

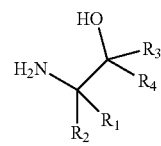

in dried chlorobenzene may be added to the solution of 4-halophthalonitrile and triflate salt in dried chlorobenzene to form a reaction mixture. An amount of the β-amino alcohol is in a range of 1-40 mmol, preferably 1-30 mmol, more preferably 1-15 mmol, and a molar ratio of 2-amino-1-propanol to 4-halophthalonitrile is in a range of 1:1 to 20:1, preferably 1:1 to 10:1, more preferably 1:1 to 5:1. The β-amino alcohol may be further substituted and comprise the aforementioned substituents on C-1, C-2, or both, and may be a chiral reagent, an achiral reagent, or a racemic mixture. Preferably, an achiral 2-amino-2-methyl-1-propanol is used. In other embodiments, a chiral ligand is prepared by employing only one of the enantiomers of 2-amino-1-propanol (or further substituted 2-amino-1-propanol), such as (S)-(+)-2-amino-1-propanol or (R)-(−)-2-amino-1-propanol.

The temperature of the reaction mixture may be raised to 80-160° C., preferably 100-160° C., more preferably 110-140° C. and may be refluxed for 12-48 hours, preferably 18-48 hours, more preferably 18-36 hours. The precursor to the ligand may be isolated and purified by methods known to those skilled in the art, such as filtration through a celite containing cartridge, aqueous work-up, extraction with organic solvents, distillation, crystallization, column chromatography, and high pressure liquid chromatography (HPLC) on normal phase or reversed phase. Preferred methods include, extraction with organic solvents and column chromatography, but are not limited to those exemplified. The yield of the precursor is at least 50%, preferably at least 75%, more preferably at least 80%.

A preparation of the ligand is described hereinafter. The precursor to the ligand, a palladium(II) salt, a base, and an arylboronic acid or an arylboronic ester may be added to a solvent and heated to a temperature in a range of 50-150° C., preferably 60-100° C., more preferably 60-80° C. for 1-48 hours, preferably 1-24 hours, more preferably 1-10 hours. Preferably, the palladium(II) salt is palladium(II) chloride, the base is potassium carbonate, and the solvent may comprise water, alcohol, toluene, dimethyl formamide, tetrahydrofuran, acetone, or mixtures thereof. Preferably, the solvent is a mixture consisting of dimethyl formamide and water and comprises 10-50 vol %, preferably 30-50 vol %, more preferably 40-50 vol % of water, based on a total volume of the solvent. A volume of the solvent may be in a range of 1-20 ml, preferably 1-10 ml, more preferably 1-5 ml. The arylboronic acid/ester comprises a hydroxy, amine, or a thiol substituent and may be further substituted with the aforementioned substituents (e.g. $R_6$). Preferably, the arylboronic acid/ester is 4-hydroxy phenylboronic acid. An amount of the precursor to the ligand may be in a range of 0.1-10 mmol, preferably 0.1-3 mmol, more preferably 0.1-1 mmol. An amount of the palladium(II) salt may be in a range of 1-20 mol %, preferably 1-10 mol %, more preferably 4-6 mol %, based on the number of moles of the precursor to the ligand. An amount of the base may be in a range of 1-10 molar equivalents, more preferably 1-5 molar equivalents, more preferably 1-3 molar equivalents of the amount of the precursor to the ligand. An amount of the arylboronic acid may be in a range of 1-10 molar equivalents, more preferably 1-2 molar equivalents, more preferably 1-1.5 molar equivalents of the amount of the precursor to the ligand. The ligand may be isolated and purified by methods known to those skilled in the art, such as filtration through a celite containing cartridge, aqueous work-up, extraction with organic solvents, distillation, crystallization, column chromatography, and high pressure liquid chromatography (HPLC) on normal phase or reversed phase. The yield of the ligand is at least 50%, preferably at least 75%, more preferably at least 80%.

A preparation of the solid-supported ligand of formula (I) is described hereinafter. A base may be added to a solution of the ligand in a dry organic solvent to form a mixture which is stirred for 1-10 hours, preferably 1-5 hours, more preferably 1-3 hours at a temperature in a range of 15-50° C., preferably 20-40° C., more preferably 20-30° C. under an inert atmosphere provided by nitrogen gas, helium gas, argon gas, or mixtures thereof. An amount of the ligand may range from 0.1-5 mmol, preferably 0.1-1 mmol, more preferably 0.1-0.5 mmol. An amount of the base may be in a range of 1-10 molar equivalents, more preferably 1-5 molar equivalents, more preferably 1-2 molar equivalents of the amount of the ligand. Preferably, the base is sodium hydride.

The solid support particle is then added to the mixture and then stirred at a temperature in a range of 40-150° C., preferably 40-100° C., more preferably 80-100° C. for 1-96 hours, preferably 1-48 hours, more preferably 10-20 hours. The solid-supported ligand may be isolated and purified by methods known to those skilled in the art, such as filtration through a celite containing cartridge. The solid-supported ligand may also be washed with solvents, such as methanol, water, acetone, and dichloromethane, and dried under reduced pressure (e.g. 0.1-50 mbar, preferably 0.1-10 mbar, more preferably 0.1-1 mbar).

A second aspect of the disclosure relates to a solid-supported catalyst, comprising a reaction product of the solid-supported ligand of the first aspect, and a palladium(II) salt of the formula $PdZ_2$, where the reaction product comprises a palladium(II) ion bound to a nitrogen atom in each oxazoline heterocycle of the ligand of formula (I), and Z is selected from the group consisting of Cl, I, Br, OAc, and OTf. The catalyst may be represented by the following formula (II):

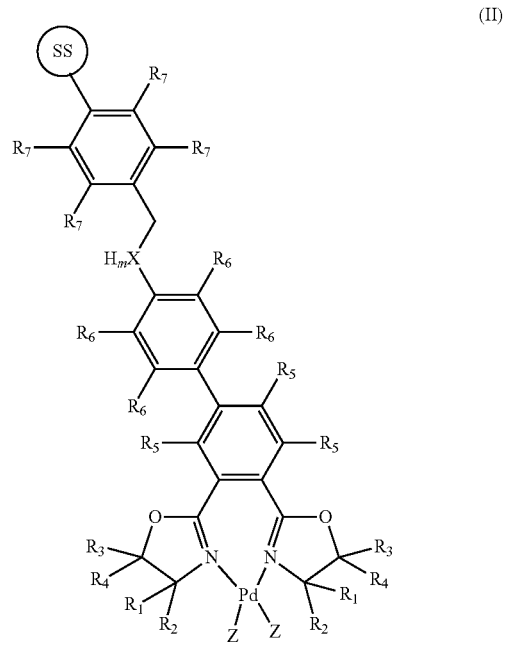

(II)

where m is 1 with the proviso that X is N, or m is 0 (i.e. no H) with the proviso that X is O or S.

In a preferred embodiment, $R_1$ and $R_2$ are $CH_3$, $R_3$, $R_4$, $R_5$, $R_6$, and $R_7$ are H, m is 0, X is O, the solid support (or SS) is silica gel, and Z is Cl.

The solid-supported catalyst comprises 0.1-1 mmol, preferably 0.1-0.6 mmol, more preferably 0.1-0.4 mmol of palladium per gram of solid-supported catalyst. The amount of palladium in the solid-supported catalyst may be determined by elemental analysis or inductively coupled plasma mass spectrometry (ICP-MS). The solid-supported catalyst has a turnover number in a range of 1,500-2,500, preferably 1,500-2,000, more preferably 1,700-2,000 and a turnover frequency in a range of 200-1,500 per hour, preferably 200-1,000 per hour, more preferably 200-500 per hour. The aforementioned values of turnover number and turnover frequency of the solid-supported catalyst may be observed when the solid-supported catalyst catalyzes any coupling reaction such as Mizoroki-Heck, Mizoroki-Heck-Matsuda, Sonogashira, Kumada, Negishi, Stille, Suzuki, Hiyama, and Buchwald-Hartwig.

A preparation of the solid-supported palladium(II) complex of formula (II) is described hereinafter. The solid-supported ligand may be suspended and stirred in a dry organic solvent (e.g. toluene, benzene, dimethyl sulfoxide, tetrahydrofuran, or mixtures thereof) for 5-120 minutes, preferably 5-90 minutes, more preferably 10-60 minutes. An amount of the ligand is in a range of 0.1-5 mmol, preferably 0.1-3 mmol, more preferably 0.1-1 mmol. A solution of a palladium(II) salt in the same solvent is added to the solid-supported ligand and the resulting mixture may be stirred at a temperature in a range of 40-150° C., preferably 40-100° C., more preferably 80-100° C. for 1-96 hours, preferably 1-48 hours, more preferably 10-20 hours. A molar ratio of the ligand to the palladium(II) salt is in a range of 1:1 to 1:2, preferably 1:1 to 2:3, more preferably 1:1 to 1:1.2. The solid-supported catalyst may also be washed with solvents, such as ethanol, methanol, water, acetone, and dichloromethane, and dried under reduced pressure (e.g. 0.1-50 mbar, preferably 0.1-10 mbar, more preferably 0.1-1 mbar).

This disclosure relates to a solid-supported palladium(II) complex for the Mizoroki-Heck coupling reactions of halides (e.g. aryl halide, benzyl halide, or vinyl halide with the halide being Cl, Br, I), triflates (e.g. aryl triflate, benzyl triflate, or vinyl triflate), or tosylates (aryl tosylate, benzyl tosylate, or vinyl tosylate) with an acrylic acid or derivatives thereof. Preferably, the solid-supported catalyst system tolerates a variety of functional groups on the halide and/or the acrylic acid and derivatives thereof. That is, the solid-supported catalyst retains the aforementioned turnover number and turnover frequency regardless of the functional groups on the halides and/or the acrylic acid and derivatives thereof. Exemplary halides, triflates, and tosylates include, without limitation, 1-bromonaphthalene, 2-bromonaphthalene, bromobenzene, 4-bromoanisole, 4-bromotoluene, 1-bromo-4-fluorobenzene, 2-bromoanisole, N-methyl-2-bromopyrrole, 3-bromoindole, 5-bromo-2-methyl-1,3-benzothiazole, 3-bromobenzofuran, 3-bromobenzothiophene, 2-bromothiophene, 2-bromothiophene, 4-bromo-3-chromene, 1-bromostyrene and (E)-2-bromostyrene, 1-bromocyclohexene, 1-bromocyclopentene, bromoethene, (E)-1-bromopropene, 2-bromopropene, iodobenzene, 1-iodonaphthalene, 2-iodonaphthalene, 4-iodoanisole, 4-iodotoluene, 4-chlorotoluene, 2-chlorotoluene, 1-chloronaphthalene, 2-chloronaphthalene, chlorobenzene, 4-chloroanisole, 2-chloroanisole, 3-chloroindole, N-methyl-2-chloropyrrole, 5-chloro-1,3-benzothiazole, 3-chlorobenzofuran, 3-chlorobenzothiophene, 2-chlorothiophene, 2-chlorothiophene, phenyl tosylate, allyl tosylate, 1-naphthyl tosylate, 2-naphthyl tosylate, phenyl tosylate, p-(ethoxycarbonyl)phenyl tosylate, p-anisyl tosylate, p-tert-butylphenyl tosylate, o-methylphenyl tosylate, o-anisyl tosylate, p-chlorophenyl tosylate, parabenzophenonyl tosylate, p-formylphenyl tosylate, 2-methylcyclohexenyl tosylate, 2-methylbenzo[d]thiazol-5-yl tosylate, 1-tosyl-1H-indol-5-yl tosylate, m-anisyl tosylate, p-(trifluoromethyl)phenyl tosylate, and p-fluorophenyl tosylate, 1-naphthyl triflate, 2-naphthyl triflate, phenyl triflate, p-(ethoxycarbonyl)phenyl triflate, p-anisyl triflate, p-tert-butylphenyl triflate, o-methylphenyl triflate, o-anisyl triflate, p-chlorophenyl triflate, parabenzophenonyl triflate, p-formylphenyl triflate, 2-methylcyclohexenyl triflate, 2-methylbenzo[d]thiazol-5-yl triflate, 1-tosyl-1H-indol-5-yl triflate, m-anisyl triflate, p-(trifluoromethyl)phenyl triflate, and p-fluorophenyl triflate, 2-thienyl and 3-thienyl triflates and their benzoderivatives, 2-furanyl and 3-furanyl triflates and their benzoderivatives, N-Boc-2-pyrrolidinyl and N-Boc-3-pyrrolidinyl triflates, cyclohexenyl triflate, 1-styryl and (E)-2-styryl triflates. Other traditional Heck cross-coupling partners (e.g. mesylates) and non-traditional Heck cross-coupling partners (e.g. alkyl halides, triflates, tosylates, etc.) are known to those of ordinary skill and may also be suitable reaction partners in the disclosed method.

The aryl halide comprises an optionally substituted aryl group which may comprise the aforementioned substituents. Preferably, the aryl group is phenyl. In a preferred embodiment, the substituents are electron-donating groups such as amino, alkoxyl, and alkyl. In another preferred embodiment, the substituents are electron-withdrawing groups such as nitro, cyano, and acetyl. The aryl group may comprise up to 5 substituents. Preferably, there is one substituent. The substituent may be located ortho, meta, or para to the halogen atom. Preferably, the substituent is located para to the halogen atom.

The aryl halide may be an aryl monohalide such as aryl chloride, aryl bromide, and aryl iodide. Preferably, the aryl monohalide is an aryl iodide such as iodobenzene. Exemplary aryl monohalide includes, without limitation, iodobenzene, 4-iodoaniline, 4-iodoacetophenone, 4-iodobenzonitrile, 4-iodoanisole, bromobenzene, 4-bromoacetophenone, and 1-iodo-4-nitrobenzene.

In another embodiment, the aryl halide is an aryl dihalide such as 1,4-dichlorobenzene, 1,4-dibromobenzene, and 1,4-diiodobenzene. Preferably, the aryl halide is 1,4-diiodobenzene.

The acrylic acid or derivatives thereof may have the following structure:

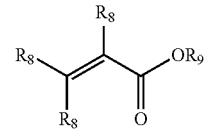

where each of $R_8$ and $R_9$ is H, an optionally substituted alkyl group, an optionally substituted aryl group, or the aforementioned substituents. The optionally substituted alkyl group may comprise 3-20 carbon atoms, preferably 4-15 carbon atoms, more preferably 6-12 carbon atoms. The optionally substituted alkyl group may be substituted with the aforementioned substituents such as cyano, halo, hydroxyl, silane and derivatives thereof, silyl ether and derivatives thereof, phenethyl, and phenylpropyl. The optionally substituted aryl group may be a phenyl group. The optionally substituted aryl group may be substituted with the aforementioned substituents such as amino, trifluromethyl, and formyl. In some embodiments, derivatives of acrylic acid include, without limitation, acrylate (e.g. sodium acrylate, zinc acrylate, zirconium acrylate, and potassium acrylate), acrylate esters (e.g. methacrylate, ethyl acrylate, n-propyl acrylate, n-butyl acrylate, n-pentyl acrylate, n-hexyl acrylate, 2-carboxyethyl acrylate, 2-(dimethylamino)ethyl acrylate, 1,1,1,3,3,3-hexafluoroisopropyl acrylate, isobornyl acrylate, ethylene glycol methyl ether acrylate, hydroxypropyl acrylate, lauryl acrylate, t-butyl acrylate, isooctyl acrylate, octadecyl acrylate, tetrahydrofurfuryl acrylate, di(ethylene glycol) 2-ethylhexyl ether acrylate, 1H,1H,2H,2H-perfluorodecyl acrylate, (E)-methyl 3-(1H-pyrazolo[3,4-b]pyridin-5-yl)acrylate, isodecyl acrylate, tridecyl acrylate, 4-tert-butylcyclohexyl acrylate, 2,2,3,3,3-pentafluoropropyl acrylate, 3,3,4,4,5,5,6,6,7,7,8,8,8-tridecafluorooctyl acrylate, 2,2,3,3,4,4,4-heptafluorobutyl acrylate, 2,2,3,3,4,4,5,5,6,6,7,7-dodecafluoroheptyl acrylate, 2,2,3,3,4,4,5,5-octafluoropentyl acrylate, 3,3,4,4,5,5,6,6,7,7,8,8,9,9,10,10,11,11,12,12,12-heneicosafluorododecyl acrylate, 3,5,5-trimethylhexyl acrylate, 2,2,3,4,4,4-hexafluorobutyl acrylate, 4-hydroxybutyl acrylate, octyl acrylate, 2-naphthyl acrylate, 2-chloroethyl acrylate, decyl acrylate, 4-acetoxyphenethyl acrylate, 2-ethylhexyl ester acrylate, 2-hydroxy-3-phenoxypropyl acrylate, 3-(dimethylamino)propyl acrylate, 10-undecenyl acrylate, 2-tetrahydropyranyl acrylate, behenyl acrylate, pentafluorophenyl acrylate, 2,2,2-trifluoroethyl acrylate), acrylamide, N-(hydroxymethyl)acrylamide, diacetone acrylamide, N-hydroxyethyl acrylamide, N-(isobutoxymethyl)acrylamide, N-(3-methoxypropyl)acrylamide, N-[tris(hydroxymethyl)methyl]acrylamide, N-(1,1,3,3-tetramethylbutyl)acrylamide, 7-[4-(trifluoromethyl)coumarin]acrylamide, 3-(4-methylphenyl)acrylamide, N-(t-butyl)acrylamide. When $R_9$ is a substituent other than hydrogen, the electrophile in the Heck coupling reaction is an acrylic ester, which is a derivative of acrylic acid. Additional derivatives of acrylic acid can also be used, such as an acrylamide, wherein —$OR_9$ in the above formula is replaced with —$NR_9R_9$.

Using the Mizoroki-Heck reaction, important compounds, such as cinnamic acid and derivatives thereof (e.g. cinammic esters or amides), can be successfully prepared. Cinnamic acid and derivatives thereof have been classified as anti-cancer agents and have been used in flavors and perfumes (Prithwiraj De, Michel Baltas, Florence Bedos-Belval, *Current Medicinal Chemistry*, 2011, 18, 1672-1703, incorporated herein by reference in its entirety). They belong to the class of auxin, which is recognized as plant hormones regulating cell growth and differentiation. In addition, cinnamic acid and derivatives thereof have been identified as anti-tuberculosis agents (Pere-Joan Cardona, "Understanding Tuberculosis—New Approaches to Fighting against Drug Resistance; Chapter 15: Cinnamic Derivatives in Tuberculosis, Published by InTech—Croatia, 2012, Page 337, incorporated herein by reference in its entirety).

In a preferred embodiment, the method comprises reacting an aryl halide (preferably aryl iodide) with an acrylic acid or derivatives thereof (preferably methacrylate or acrylamide) in the presence of a solvent, a base (preferably potassium hydroxide), and the solid-supported catalyst of formula (II) at a temperature in a range of 35-110° C., thereby forming the cinnamic acid or derivatives thereof.

In some embodiments, prior to the reacting, the method further comprises an adding step where the solid-supported catalyst is added to the organic solvent, followed by the reactants, the base, and water to form a reaction mixture. In another embodiment, the base is first dissolved in water to form a basic solution, which is then added to the other compounds in the organic solvent. In one embodiment, the solid-supported catalyst is not preformed but is formed in situ in a reaction flask (i.e. at least one of the aforementioned palladium(II) salts and the solid-supported ligand are added to the reaction flask separately). Preferably, the adding step is performed in air. In another embodiment, the adding step is performed in an inert atmosphere provided by an inert gas such as argon, nitrogen, helium, or mixtures thereof.

The solvent may comprise 5-95% by volume of water and 5-95% by volume of an organic solvent, based on a total volume of the solvent. Preferably, the solvent comprises 30-70% by volume of water and 30-70% by volume of an organic solvent, based on the total volume of the solvent. Most preferably, the solvent consists of 50% by volume of water and 50% by volume of the organic solvent, based on the total volume of the solvent. Preferably, deionized distilled water is used. Preferably, the organic solvent is dimethyl formamide.

The aryl halide is the limiting reagent in the coupling reaction. An amount of the aryl halide may be in a range of 0.5-20 mmol, preferably 0.5-10 mmol, more preferably 0.5-5 mmol. An amount of the acrylic acid or derivatives thereof may be in a range of 0.5-100 mmol, preferably 0.5-50 mmol, more preferably 0.5-25 mmol, or 1-5 molar equivalents, preferably 1-3 molar equivalents, more preferably 1-2 molar equivalents of the amount of aryl halide. An amount of the base may be in a range of 0.5-100 mmol, preferably 0.5-50 mmol, more preferably 1-25 mmol, or 1-5 molar equivalents, preferably 1-3 molar equivalents, more preferably 2-3 molar equivalents of the amount of aryl halide.

An amount of the solid-supported catalyst may range from 0.05-10 mol % of a number of moles of the aryl halide, more preferably 0.2-2 mol %, more preferably 0.2-1 mol %. Although higher catalyst loadings (e.g. up to 20 mol %, 30 mol %, 40 mol %, 80 mol %) may be used and the method will still proceed as intended.

The reacting may be performed at a temperature in a range of 35-110° C., preferably 50-110° C., more preferably 70-100° C. An external heat source, such as a water bath or an oil bath, an oven, microwave, or a heating mantle, may be employed to heat the reaction mixture. In a preferred embodiment, the external heat source is a thermostatted thermocirculator. In one embodiment, the aqueous solution is not heated with microwave irradiation. Preferably, the reacting is performed in air. In another embodiment, the reacting is performed in an inert atmosphere provided by the aforementioned inert gases.

A duration of the reaction may range from 0.5-24 hours, preferably 1-12 hours, more preferably 4-8 hours. The reaction may be shaken/stirred throughout the duration of the reaction by employing a rotary shaker, a magnetic stirrer, or an overhead stirrer. In another embodiment, the reaction mixture is left to stand (i.e. not stirred). In one embodiment, the reaction mixture is preferably mixed in a centrifugal mixer with a rotational speed of at least 500 rpm, preferably at least 800 rpm, more preferably at least 1,000 rpm, even though it can also be mixed with a spatula. In one embodiment, the reaction mixture is sonicated during the mixing.

The reaction mixture is preferably heterogeneous and comprises suspended solid-supported catalyst particles in the liquid reaction mixture. In one embodiment, the solid-supported catalyst particles are dispersed within the reaction mixture, and may further be filtered and recycled at the end of the reaction. In one embodiment, the solid-supported catalyst is placed in a bag and the bag is immersed in the reaction mixture. Accordingly, the solid-supported catalyst remains in the bag until the coupling reaction is completed.

The progress of each reaction may be monitored by methods known to those skilled in the art, such as thin layer chromatography, gas chromatography, nuclear magnetic resonance, infrared spectroscopy, and high pressure liquid chromatography combined with ultraviolet detection or mass spectroscopy. Preferably, thin layer chromatography and gas chromatography combined with mass spectroscopy are used.

Under the basic reaction conditions, cinnamate (instead of cinnamic acid) and derivatives thereof may be obtained. The cinnamate and derivatives thereof may be converted to the acid form by adding a mineral acid (e.g. hydrochloric acid, sulfuric acid, and phosphoric acid) during the reaction work up.

The compounds obtained by the method of the present disclosure are isolated and purified by employing the aforementioned methods which are well-known to those skilled in the art. The isolated yield of the cinnamic acid or derivatives thereof is at least 80%, preferably at least 90%, more preferably at least 92%, based on the initial number of moles of the aryl halide. The cinnamic acid or derivatives thereof, resulting either from a single run or a combination of runs, comprises less than 10 ppb palladium (measured by ICP-MS), preferably less than 5 ppb, more preferably less than 1 ppb, based on a total weight of the cinnamic acid or derivatives thereof.

In some embodiments, the method further comprises separating the solid-supported catalyst from the cinnamic acid or derivatives thereof, followed by recycling the used solid-supported catalyst. The solid-supported catalyst may be separated by removing the bag of solid-supported catalyst, dialysis in a solvent, or using a micro-filter or a paper filter.

The phrase "recycling the solid-supported catalyst" refers to a process whereby the solid-supported catalyst is first washed by an organic solvent, dried, and then added to a new batch of reactants (either for the same or a different type of coupling reaction). Preferred organic solvents for washing the solid-supported catalyst and/or dialysis may include, without limitation, methanol, acetone, ethanol, tetrahydrofuran, acetonitrile, dichloromethane, ether, glycol ether, acetamide, dimethyl acetamide, dimethyl sulfoxide, or combinations thereof. The solid-supported catalyst may be dried in vacuum, and/or with heating, for example, the catalyst may be dried in a vacuum oven. Dried solid-supported catalyst may be stored in a desiccator until the next run.

In one embodiment, the solid-supported catalyst is recycled for at least 2 runs, preferably at least 10 runs, more preferably at least 20 runs, even more preferably at least 30 runs. The catalyst may lose less than 5 wt %, preferably less than 2 wt %, more preferably less than 0.1 wt % of palladium (based on an initial amount of palladium present in the solid-supported catalyst) after the solid-supported catalyst is used for at least 2 runs, preferably at least 10 runs, more preferably at least 20 runs, even more preferably at least 30 runs. The yield of the coupling reaction may decrease less than 20 percentage points, preferably less than 10 percentage points, more preferably 5 percentage points after the solid-supported catalyst is used for at least 2 runs, preferably at least 10 runs, more preferably at least 20 runs, even more preferably at least 30 runs. The turnover number and the turnover frequency of the solid-supported catalyst may decrease less than 10%, preferably less than 5%, more preferably less than 2% after the solid-supported catalyst is used for at least 2 runs, preferably at least 10 runs, more preferably at least 20 runs, even more preferably at least 30 runs.

Having generally described this disclosure, a further understanding can be obtained by reference to certain specific examples which are provided herein for purposes of illustration only and are not intended to be limiting unless otherwise specified.

Example 1 Reagents and Experimental Methods

Materials for the synthesis of the solid-supported ligand and palladium complex were purchased from Sigma-Aldrich and were used as received. All solvents used in the synthesis were distilled before their use. 4-Benzyl chloride functionalized silica gel (200-400 mesh, extent of labelling: 1.2 mmol/g loading) was purchased from Sigma-Aldrich.

Solid state NMR spectral data was recorded using CP-MAS on a Bruker Avance 400 MHz machine. IR spectra were recorded in wavenumbers ($cm^{-1}$) using FT-IR spectrometer (Perkin-Elmer 16F model). Elemental analyses were performed on Perkin Elmer Series 11 (CHNS/O) Analyzer 2400. Palladium loading was estimated using inductively coupled plasma mass spectrometer, X-series 2 ICP-MS, thermos scientific. Thermal stability of the solid-supported ligands and complexes were established using thermogravimetric (TG) (Perkin-Elmer TGA 7, US) analysis at a heating rate of $10°$ C. $min^{-1}$ through to $700°$ C. under nitrogen atmosphere. The morphology of the supports, solid-supported ligands and solid-supported complexes were studied using scanning electron microscope, JEOL JSM6610LV SEM.

Example 2 Synthesis of Precursor to Ligand, 2,2'-(4-Iodobenzene-1,2-diyl)-bis(4,4-dimethyl-4,5-dihydro-1,3-oxazole) (BOX-1)

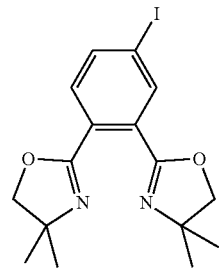 [SMILES: CC1(C)COC(c2ccc(I)cc2C2=NC(C)(C)CO2)=N1]

The precursor to the ligand was prepared using an earlier published procedure (M. B. Ibrahim, B. El Ali, M. Fettouhi, L. Ouahab, Appl. Organometal. Chem, 2015, 29, 400, incorporated herein by reference in its entirety). A solution of 4-iodophthalonitrile (4.0 mmol) and zinc triflate (5.0 mol %, 0.2 mmol) in dried chlorobenzene (30 mL) was stirred at room temperature for 15 minutes. A solution of 2-amino-2-methyl-1-propanol (8.0 mmol) in dry chlorobenzene (5 mL) was slowly added. The temperature was raised to $135°$ C. and the reaction mixture was refluxed for 24 hours. The solvent was removed using a rotary evaporator. The crude product was dissolved in 30 mL of dichloromethane and extracted twice with distilled water (2×20 mL). The aqueous layer was then separated and the combined organic layers were dried with anhydrous sodium sulfate. The dichloromethane was removed using a rotary evaporator to obtain the impure product, which was then purified using silica gel column chromatography with dichloromethane/ether (4/1) as eluent.

Example 3 Synthesis of Hydroxyl Functionalized bis(oxazoline) Ligand, 3,4-bis(4,4-dimethyl-4,5-dihydro-1,3-oxazol-2-yl)biphenyl-4-ol (BOX-OH)

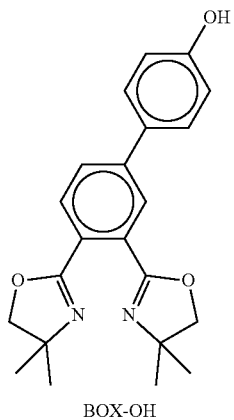

BOX-OH

The synthesis of hydroxyl functionalized BOX ligand (BOX-OH) has been previously described (U.S. provisional patent application 62/313,849, incorporated herein by reference in its entirety).

2,2'-(4-Iodobenzene-1,2-diyl)-bis(4,4-dimethyl-4,5-dihydro-1,3-oxazole) (BOX-1) (0.50 mmol), PdCl$_2$ (0.025 mmol, 5.0 mol %), K$_2$CO$_3$ (1.0 mmol, 2.0 mol equivalent), DMF (2 mL), distilled water (2 mL) and the 4-hydroxy phenylboronic acid (0.6 mmol), were added in a 10 mL round bottom flask. The mixture was stirred at 70° C. for 6 h. After completion of the reaction, the mixture was cooled down and acidified with 1M HCl. The acidified solution was extracted 3 times with EtOAc and the combined EtOAc extract was dried using anhydrous MgSO$_4$. The solvent was removed under reduced pressure and the product was purified by silica gel column chromatography using hexane-EtOAc (1:9) as an eluent.

Example 4 Synthesis of Solid-Supported bis(oxazoline) Ligand (BOX-Si)

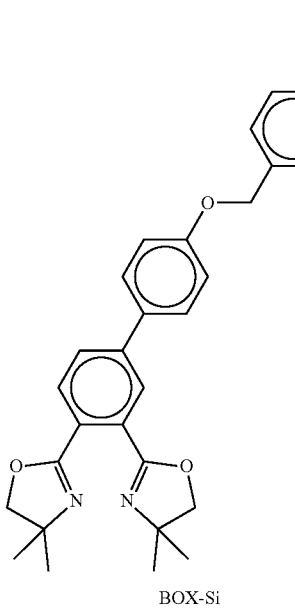

BOX-Si

BOX-OH reacted with the benzyl silica support to form the silica immobilized BOX ligand (BOX-Si).

NaH (0.50 mmol) was added in one portion to a stirred solution of 3,4-bis(4,4-dimethyl-4,5-dihydro-1,3-oxazol-2-yl)biphenyl-4-ol (BOX-OH) (0.31 mmol) in dry DMF in a dry flask. The mixture was stirred for 2 h at room temperature and under argon atmosphere. The benzyl silica support (0.30 mmol) was added and the mixture was stirred at 90° C. for 12 h. The solid product was filtered and washed successively with methanol, water, acetone and dichloromethane. The product, benzyl silica-supported BOX ligand (BOX-Si), was dried at room temperature under vacuum.

It is worth mentioning that the ether bond was considered stable and suitable for linking the ligand to the silica support. Whereas most functional groups such as esters and amides can easily be hydrolyzed under the standard conditions of coupling reactions, which involves the use of bases such as KOH and K$_2$CO$_3$ and also heat. The ether linkage is particularly stable to the reaction conditions and thus, expected to prevent leaching of the ligand during the catalytic application.

Example 5 General Procedure for the Synthesis of Benzyl Silica-Supported palladium(II) bis(oxazoline) Catalyst (Pd-BOX-Si)

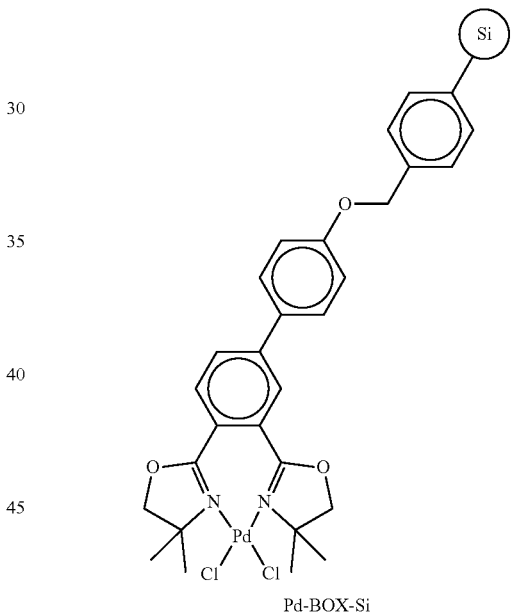

Pd-BOX-Si

The silica immobilized BOX ligand was further reacted with bis(benzonitrile) palladium(II) chloride to produce the silica-supported palladium(II)-bis(oxazoline) catalyst (Pd-BOX-Si).

The silica-supported bis(oxazoline) ligand (BOX-Si) (0.30 mmol, 0.25 g) was stirred in anhydrous toluene for 30 min. A solution of bis(benzonitrile) palladium(II) chloride (0.30 mmol, 0.12 g) in toluene was added and the resulting mixture was stirred at 90° C. for 12 h. The solid product, benzyl silica-supported palladium(II) bis(oxazoline) catalyst (Pd-BOX-Si), was filtered, washed thoroughly with ethanol and dried in a vacuum.

The metal loading of the solid-supported palladium catalyst, which was determined using ICP-MS, was found to be 2.8% and equivalent to 0.30 mmol/g. The palladium loading of the silica-supported dichloridopalladium(II) bis(oxazoline) catalyst was determined using ICP-MS and was found to be 2.8%. This corresponds to 0.3 mmol palladium per gram of the solid-supported catalyst.

The formation of Pd-BOX-Si was confirmed by Fourier transform infrared spectroscopy (FT-IR), solid-state cross-polarization magic angle spinning carbon-13 nuclear magnetic resonance (CP-MAS $^{13}$C NMR), elemental analysis and inductively coupled plasma mass spectrometry (ICP-MS). The Pd-BOX-Si was further characterized with scanning electron microscopy (SEM) and thermogravimetric analysis (TGA).

Example 6 Characterization of Silica-Supported bis(oxazoline) Ligand (BOX-Si) and palladium(II) (Pd-BOX-Si) Catalyst Using FT-IR FT-IR analysis of the silica-supported bis(oxazoline) ligand reveals a strong band at 1661 cm$^{-1}$ (FIG. 1). This band was initially absent in the unmodified benzyl silica support (FIG. 1). This band reflects —C=N— stretching in the oxazoline ring. The appearance of this additional band is an indication that the BOX ligand has been incorporated into the silica support matrix. The —C=N— stretching band shifted to 1643 cm$^{-1}$ on complexation with palladium (FIG. 1).

Figure 2:
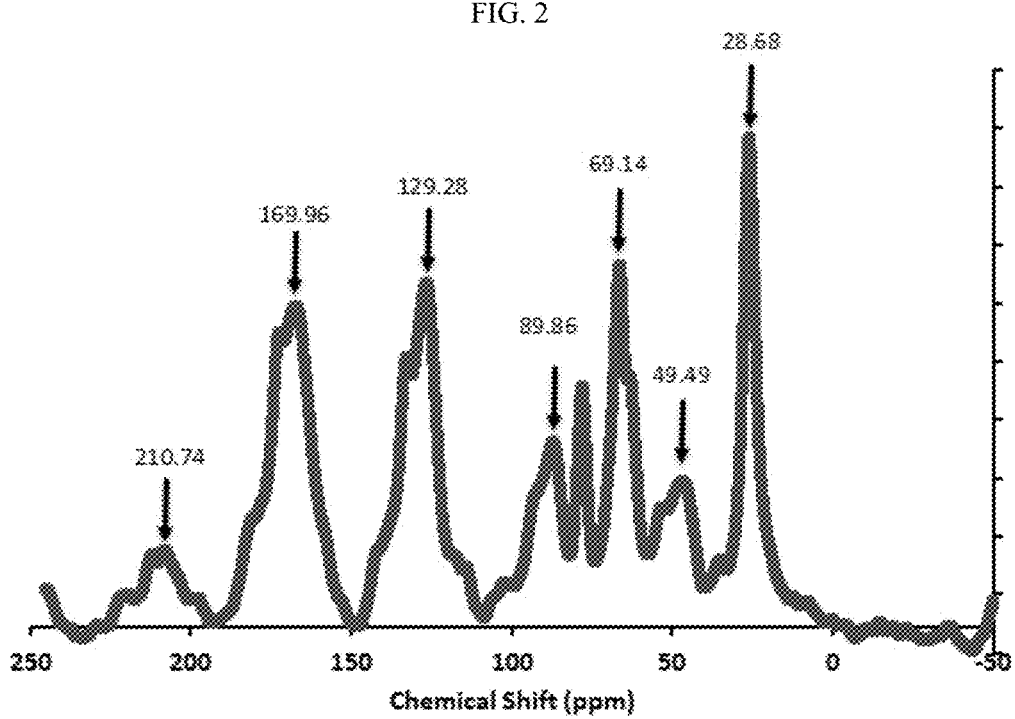
FIG. 2 is a cross-polarization magic angle spinning (CP-MAS) $^{13}$C NMR spectrum of the silica-supported BOX ligand.
Figure 3:
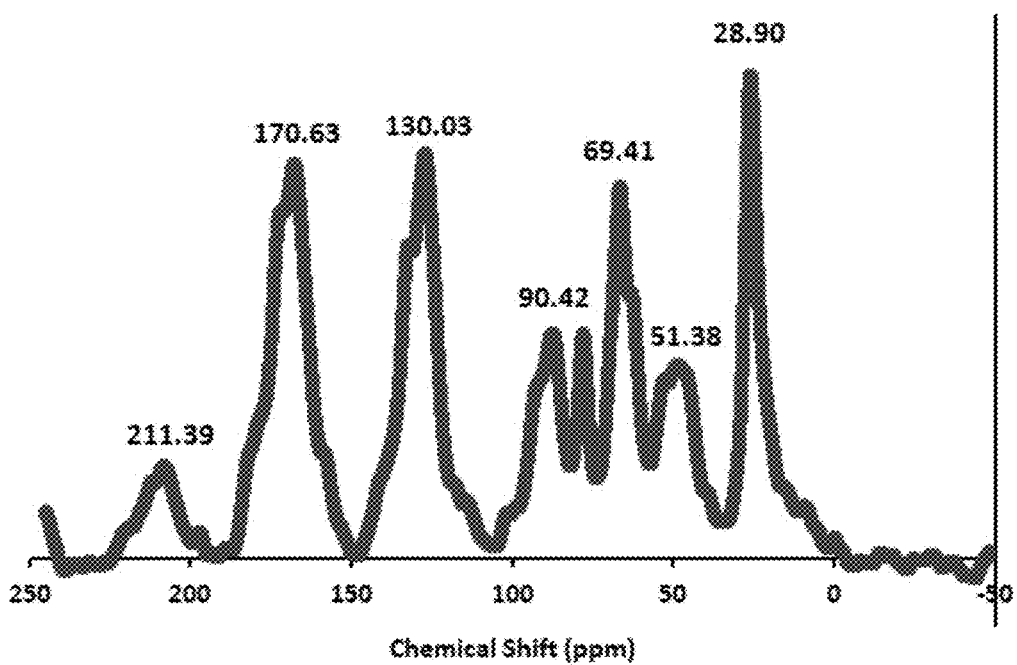
FIG. 3 is a CP-MAS $^{13}$C NMR spectrum of the silica-supported Pd-BOX catalyst.

Example 7 Characterization of Silica-Supported BOX Ligand (BOX-Si) and palladium(II) (Pd-BOX-Si) Catalyst Using CP-MAS $^{13}$C NMR The silica-supported ligand and palladium(II) complex were further characterized using solid state $^{13}$C NMR. The spectra of the silica bound ligand (FIG. 2) and its palladium (II) complex (FIG. 3) were in entire agreement with those reported for other known bis(oxazoline) and solid-supported bis(oxazoline) ligands and their complexes. For instance, the resonance due to imino carbon (—C=N) was observed at 169.96 ppm in the spectrum of the silica-supported ligand. This band slightly shifted to 170.63 ppm after complexation. The CP-MAS spectra of both the solid-supported ligand and complex showed that the signals for the carbon atoms of the two bis(oxazoline) rings are no longer symmetric comparing to the free ligand and complex.

Figure 4:
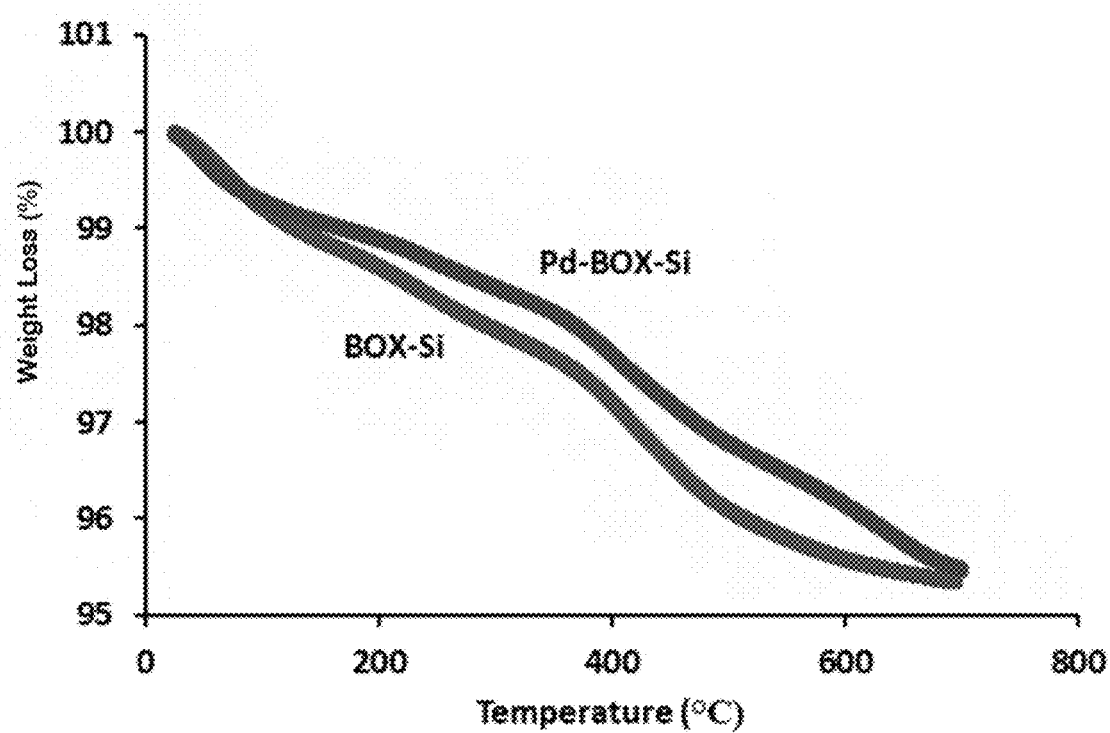
FIG. 4 is an overlay of thermogravimetric curves of the silica-supported BOX ligand "BOX-Si" and the silica-supported Pd-BOX catalyst "Pd-BOX-Si".

Example 8 Analysis of Silica-Supported palladium(II)-BOX (Pd-BOX-Si) Catalyst Using TGA The thermal stability for the palladium(II) catalyst (Pd-BOX-Si) was determined using TGA (FIG. 4). The Pd-BOX-Si was found to possess high thermal stability with a decomposition temperature of 150° C.

Figure 5:
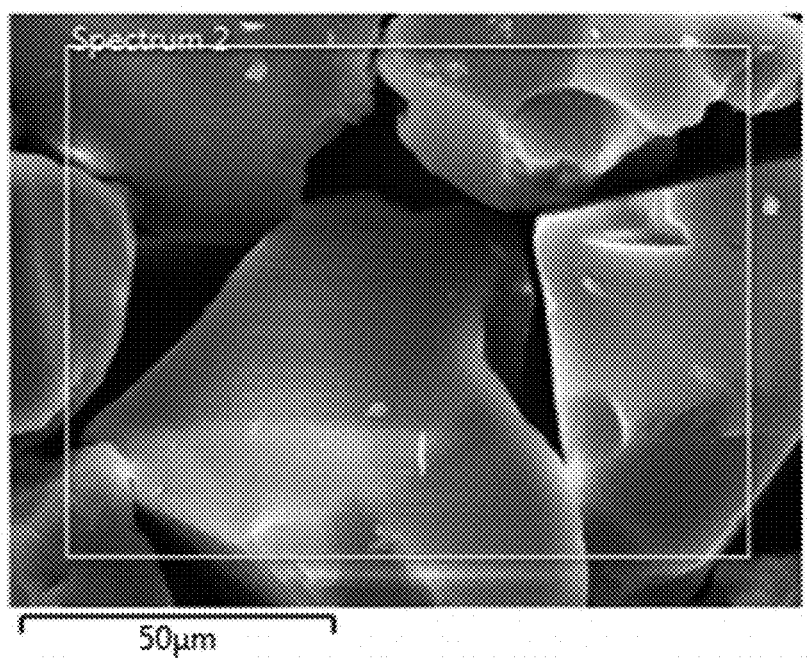
FIG. 5 is a scanning electron micrograph of the unmodified 4-benzyl chloride functionalized silica support.
Figure 6:
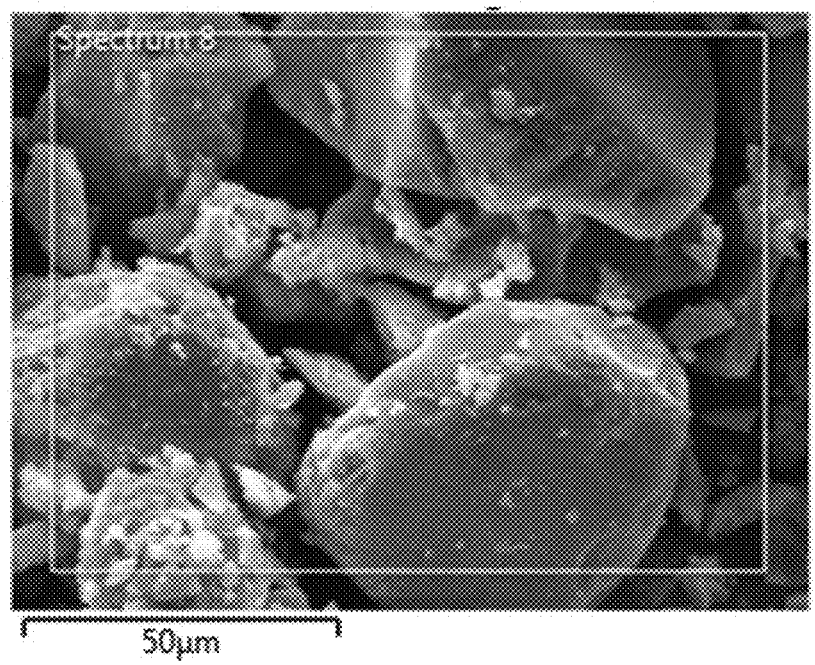
FIG. 6 is a scanning electron micrograph of the silica-supported BOX ligand.
Figure 7:
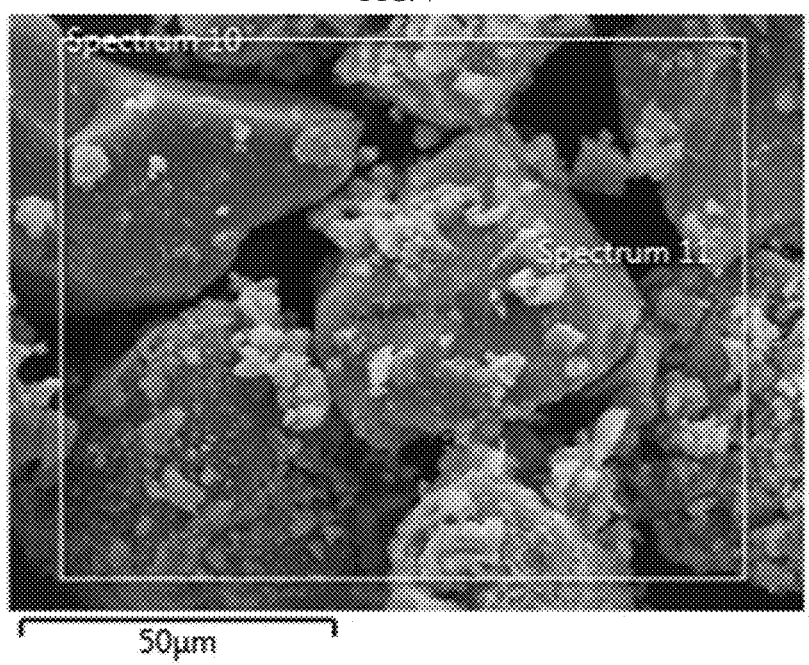
FIG. 7 is a scanning electron micrograph of the silica-supported Pd-BOX catalyst.

Example 9 Analysis of Silica-Supported BOX Ligand (BOX-Si) and palladium(II) (Pd-BOX-Si) Catalyst Using SEM In order to assess the morphology of the 4-benzyl chloride functionalized silica support, the silica-supported BOX ligand and palladium(II) catalyst, SEM micrographs were recorded for a pure benzyl chloride silica support, silica-supported bis(oxazoline) ligand (BOX-Si) and silica-supported palladium(II)-bis(oxazoline) catalyst (Pd-BOX-Si). As expected, the smooth and flat surfaces of the 4-benzyl chloride functionalized silica support (FIG. 5), have been broken to a rough and irregular surface after incorporation of the metal complex (FIG. 7) (Trilla, M.; Pleixats, R.; Wong Chi Man, M.; Bied, C.; Moreau, J. J. E. *Tetrahedron Lett.* 2006, 47, 2399; Trilla, M.; Pleixats, R.; Wong Chi Man, M.; Bield, C.; Moreau, J. J. E. *Adv. Synth. Catal.* 2008, 350, 577; Gruber-Woelfler, H.; Radaschitz, P. F.; Feenstra, P. W.; Haas, W.; Khinas, J. G. *J. Catal.* 2012, 286, 30; and Antony, R.; Tembe, G. L.; Ravindranathan, M.; Ram, R. N. *J. Appl. Polym. Sci.*, 2003, 90, 370, each incorporated herein by reference in their entirety).

Example 10 Characterization of Silica-Supported palladium-bis(oxazoline) (Pd-BOX-Si) Catalyst Using X-Ray Photoelectron Spectroscopy (XPS)

Figure 8:
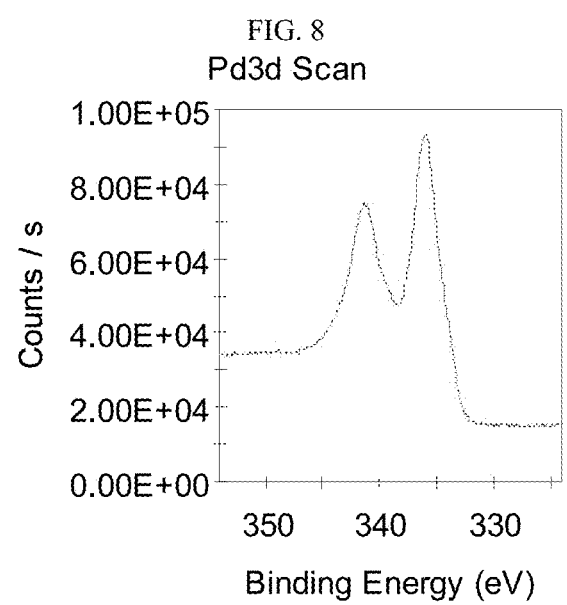
FIG. 8 is a XPS spectrum of the fresh silica-supported Pd-BOX catalyst, showing Pd 3d.

In the XPS spectrum of Pd-BOX-Si catalyst (FIG. 8), palladium peaks were observed in the range of 335 to 342 eV. Two distinctive 3d peaks were identified. The first peak with binding energy of 336.08 eV (Pd 3d$_{5/2}$) and the second peak with binding energy 341.38 (Pd 3d$_{3/2}$). The data is consistent with palladium(II) forms, and this confirmed that palladium(II) is the main form of palladium in the solid-supported catalyst (Yeap, H. N; Mian, W.; Hong, H.; Christina, L. L. C. *Chem. Commun.*, 2009, 5530; and Hajipour, A. R.; Shirdashtzade, Z.; Azizi, G. *J. Chem. Sci.*, 2014, 126, 1, 85, each incorporated herein by reference in their entirety).

Example 11 Catalytic Activities of Silica-Supported palladium-bis(oxazoline) (Pd-BOX-Si) in Mizoroki-Heck Coupling Reaction The catalytic activity of the new silica-supported palladium-bis(oxazoline) catalyst in Mizoroki-Heck coupling reaction of various olefins and aryl halides was carefully studied. The cross-coupling reactions of various aryl halides with acrylic acid, methacrylate and acrylamide were considered.

Figure 10:
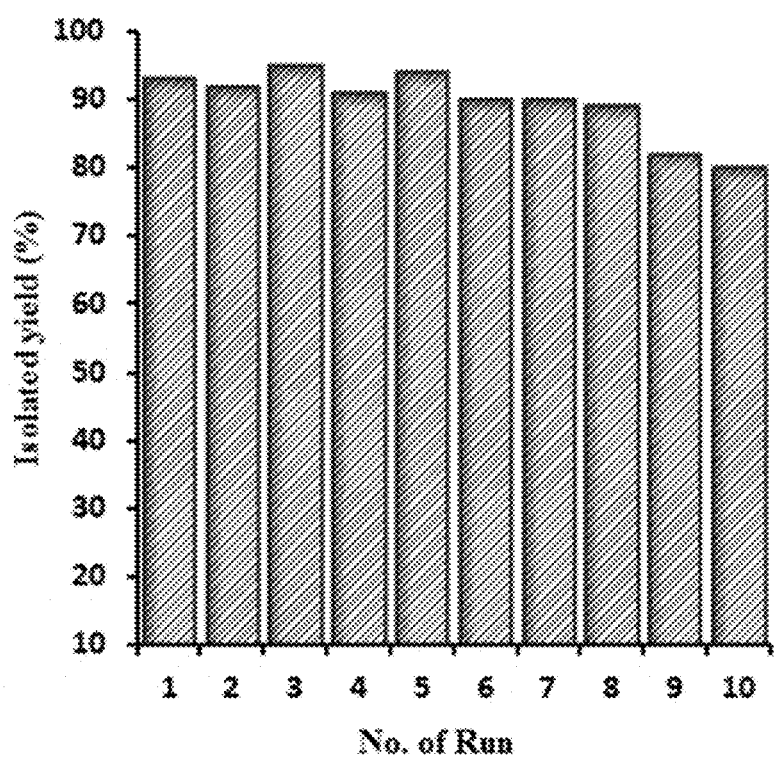
FIG. 10 is a graph showing the isolated yields of cinnamic acid formed in the presence of recycled silica-supported Pd-BOX catalyst, which was recycled after each run and used in the subsequent run.

The recycling ability of the new silica-supported palladium-bis(oxazoline) catalysts in Mizoroki-Heck coupling reaction of iodobenzene with methacrylate was investigated (Equation 1 and FIG. 10). Interestingly, the solid-supported catalyst was recycled up to ten times without significant loss in catalytic activity. The turnover number of the silica-supported palladium-bis(oxazoline) catalyst was estimated for the 10 runs as 1800, while the turnover frequency was found to be 300/h. In order to confirm the efficiency of the solid-supported palladium-bis(oxazoline) catalyst, an experiment with a ratio of iodobenzene (10.0 mmol) to solid-supported palladium-bis(oxazoline) catalyst (0.005 mmol) equal to 2,000 was left to react for 6 hours. A complete conversion of iodobenzene and excellent isolated yield of product 3aa (93%) was observed. The turnover number of the solid-supported palladium-bis(oxazoline) catalysts in the later experiment was estimated as 1,860, while the turnover frequency was found as 310/h.

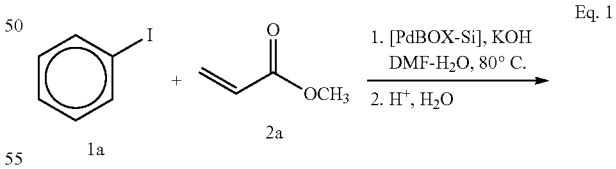

Eq. 1

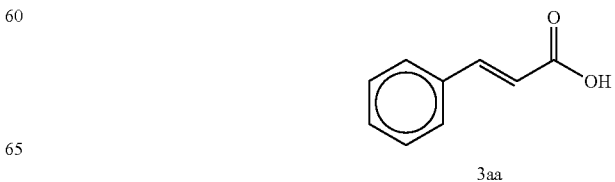

3aa

Example 12 Mizoroki-Heck Coupling Reaction of Various Acrylates with Aryl Halides Catalyzed by Silica-Supported palladium-bis(oxazoline) (Pd-BOX-Si) Catalyst The Mizoroki-Heck coupling of a broad range of substrates using DMF-$H_2O$ (1:1) as a solvent system and KOH as a base (Equation 2) was performed. Thus, various aryl halides including aryl iodides and aryl bromides were coupled successfully with various with different acrylates (Table 1). The silica-supported catalyst was used in the coupling of aryl halides with acrylate, acrylic acid and acrylamide. At the end of each reaction, the catalyst was removed from the reaction mixture and dialyzed in DMF to remove all traces of reactants and products before taking it to the next catalytic run.

The coupling reactions of aryl halides with methacrylate, acrylic acid and acrylamide were investigated (Table 1). Under the reaction conditions, the acrylates and acrylamides were hydrolyzed to the corresponding salts of the carboxylic acids. The aryl propenoic acids were obtained after acidic work up. Aryl iodides having either activating or deactivating groups reacted smoothly with acrylates to give the cross coupling products in excellent isolated yields (90-96%) (Table 1, entries 1-7). The coupling reactions of aryl bromides were conducted at 100° C., using a fresh catalyst and without dialysis bag. Also, high isolated yields of the coupling products were obtained (84-88%) (Table 1, entries 8-10).

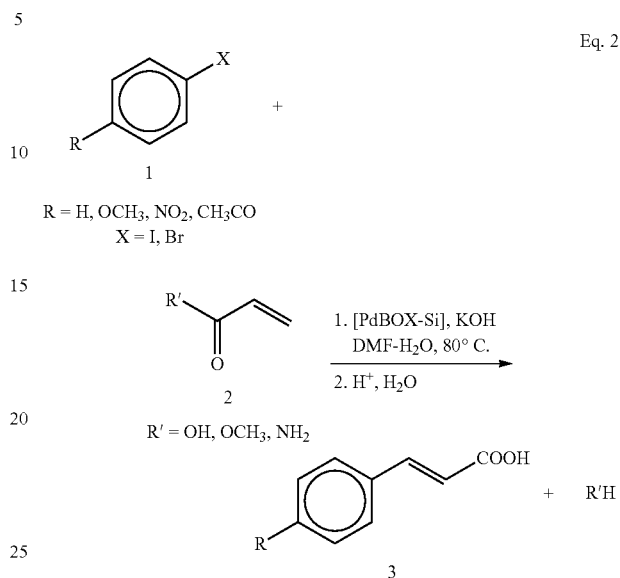

Eq. 2

R = H, $OCH_3$, $NO_2$, $CH_3CO$
X = I, Br

R' = OH, $OCH_3$, $NH_2$

1. [PdBOX-Si], KOH DMF-$H_2O$, 80° C.
2. $H^+$, $H_2O$

TABLE 1

Mizoroki-Heck coupling reactions of acrylates with aryl halides using silica-supported palladium bis(oxazoline) (Pd-BOX-Si) catalyst.[a]

| Entry | Aryl halide 1 | | Alkene 2 | | Coupling Product 3 | | Yield (%)[b] |
|---|---|---|---|---|---|---|---|
| 1 | C6H5-I | 1a | CH2=CH-C(O)OCH3 | 2a | PhCH=CH-COOH | 3aa | 91 |
| 2 | | 1a | CH2=CH-COOH | 2b | PhCH=CH-COOH | 3ab | 96 |
| 3 | | 1a | CH2=CH-C(O)NH2 | 2c | PhCH=CH-COOH | 3ac | 90 |
| 4 | 4-NO2-C6H4-I | 1b | | 2a | 4-NO2-C6H4-CH2CH2-COOH | 3ba | 91 |
| 5 | | 1b | | 2b | 4-NO2-C6H4-CH=CH-COOH | 3bb | 94 |

TABLE 1-continued

Mizoroki-Heck coupling reactions of acrylates with aryl halides using silica-supported palladium bis(oxazoline) (Pd-BOX-Si) catalyst.[a]

| Entry | Aryl halide 1 | Alkene 2 | Coupling Product 3 | | Yield (%)[b] |
|---|---|---|---|---|---|
| 6 | 4-MeO-C6H4-I | 2a | 4-MeO-C6H4-CH=CH-COOH | 3ca | 90 |
| 7 | 1c | 2b | 4-MeO-C6H4-CH=CH-COOH | 3cb | 93 |
| 8[c] | C6H5-Br | 1d | 2a | C6H5-CH=CH-COOH | 3aa | 84 |
| 9[c] | 1d | 2b | C6H5-CH=CH-COOH | 3aa | 80 |
| 10[c] | 4-acetyl-C6H4-Br | 1e | CH2=CH-COOH | 4-acetyl-C6H4-CH=CH-COOH | 3eb | 88 |

[a]Reaction conditions: [Pd-BOX-Si] (0.0050 mmol), alkene (1.5 mmol), aryl halide (1.0 mmol), KOH (2.0 mmol), DMF (3.0 mL), $H_2O$ (3.0 mL), 80° C., 6 h, acid workup.
[b]Isolated yield.
[c]100° C.

Example 13 Characterization of the Used Solid-Supported palladium-bis(oxazoline) Catalysts The ability to reuse the solid-supported palladium-bis(oxazoline) catalysts several times and in various reactions without significant loss in their catalytic activities demonstrates their high stabilities. The interesting results realized with the solid-supported catalysts urged the inventors to carry out further investigations to asses any change in the structure of the used catalysts in comparison with the unused catalysts. The catalysts recovered after the 12$^{th}$ run of the Suzuki coupling reaction and the 10$^{th}$ run of both the Mizoroki-Heck and the Sonogashira coupling reactions were washed successively with distilled water, acetone and methanol. The catalysts were then dried in an oven at 100° C. prior to analysis. The purified catalysts were analyzed with FT-IR, XPS and the amount of palladium was established using ICP-MS.

Example 14 Characterization of the Used Silica-Supported palladium-bis(oxazoline) (Pd-BOX-Si) Catalyst Using FT-IR The catalyst was pressed into pellets with KBr and analyzed using FT-IR. The FT-IR spectrum for the recovered silica-supported palladium-bis(oxazoline) (Pd-BOX-Si) (FIG. 1) catalyst was found to be similar with the spectrum of the unused (fresh) catalyst.

Example 15 Analysis of the Used Silica-Supported palladium-bis(oxazoline) (Pd-BOX-Si) Catalyst Using ICP-MS The percentage of palladium on Pd-BOX-Si recovered from the Mizoroki-Heck coupling reaction of iodobenzene with methacrylate was found to be 2.4%, which is similar to the amount of palladium on the fresh catalyst (2.8%). This result further justifies the high recycling ability observed with the new silica-supported palladium-bis(oxazoline) catalyst.

Figure 9:
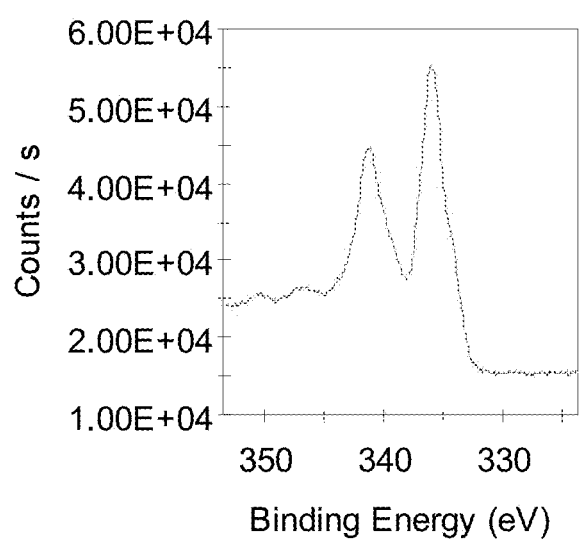
FIG. 9 is a XPS spectrum of the used silica-supported Pd-BOX catalyst, showing Pd 3d.

Example 16 Analysis of the Used Solid-Supported palladium-bis(oxazoline) Catalysts Using XPS The XPS spectra of the used silica-supported palladium-bis(oxazoline) catalyst (Pd-BOX-13) (FIG. 9) recovered after the tenth run of the Mizoroki-Heck coupling reaction showed that the oxidation state of palladium remained unchanged after the catalysis. Similar to the unused (fresh) solid-supported catalysts, the 3d spectrum resolved into $3d_{5/2}$ and $3d_{3/2}$ spin orbit pairs with binding energies 334.58 eV and 339.78 eV (Pd-BOX-Si) and 336.18 and 341.68 (Pd-BOX-13) respectively.

Example 17 Palladium Leaching Test

The main objective of supporting a catalyst is to ease its separation from the product and to minimize the level of contamination caused by the toxic metal. The leaching of palladium into the products was analyzed using ICP-MS. After the tenth run of the Mizoroki-Heck coupling reaction, a sample from each run of the coupling reaction was taken for the analysis and digested using concentrated nitric acid. In addition, the products of the 10 runs were combined, digested using concentrated nitric acid. All samples were analyzed by ICP-MS.

The results of the ICP-MS analysis indicated that the concentration of palladium in the combined products was below 10 ppb. These results indicated that less than 0.5% of the total palladium on the solid-supported catalysts was leached into the products. These results clearly indicated the high stability of the solid-supported catalysts towards the cross-coupling reactions under the prescribed reaction conditions.

The invention claimed is:

1. A method for synthesizing cinnamic acid, the method comprising:
    reacting an aryl halide with an acrylic acid in the presence of a solvent, a base, and a solid-supported catalyst of formula (II) at a temperature in a range of 35-110° C., thereby forming the cinnamic acid:

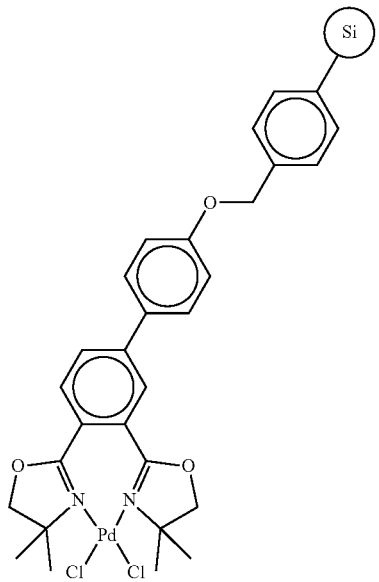

(II)

wherein Si is a solid silica support.

2. The method of claim 1, further comprising:
    separating the solid-supported catalyst from the cinnamic acid; and
    reusing the solid-supported catalyst in at least two cycles, wherein the solid-supported catalyst loses less than 5 wt % of the palladium after the at least two cycles.

3. The method of claim 1, wherein the aryl halide is a limiting reactant.

4. The method of claim 1, wherein an amount of the solid-supported catalyst is in a range of 0.05-10 mol % relative to a number of moles of the aryl halide.

5. The method of claim 1, wherein the solvent comprises 5-95% by volume of water and 5-95% by volume of an organic solvent, based on a total volume of the solvent.

* * * * *